US006103466A

United States Patent [19]
Grobet et al.

[11] Patent Number: 6,103,466
[45] Date of Patent: Aug. 15, 2000

[54] DOUBLE-MUSCLING IN MAMMALS

[75] Inventors: Luc Grobet, Esneux; Michel Georges, Villers-aux-Tours, both of Belgium

[73] Assignee: University of Liege, Liege, Belgium

[21] Appl. No.: 08/891,789

[22] Filed: Jul. 14, 1997

[51] Int. Cl.$^7$ .............................. C12Q 1/68; C12P 19/34; C07H 21/02

[52] U.S. Cl. ........................... 435/6; 435/91.1; 435/91.2; 536/23.1; 536/24.3

[58] Field of Search ............................ 435/6, 91.2, 91.1; 536/24.3, 23.1

[56] References Cited

U.S. PATENT DOCUMENTS

| | | | |
|---|---|---|---|
| 4,736,866 | 4/1988 | Leder et al. | 800/1 |
| 4,816,397 | 3/1989 | Boss et al. | 435/68 |
| 4,816,567 | 3/1989 | Cabilly et al. | 530/387 |
| 4,870,009 | 9/1989 | Evans et al. | 435/70 |
| 5,264,558 | 11/1993 | Kim et al. | 530/402 |
| 5,288,630 | 2/1994 | Wathen | 435/240.2 |
| 5,643,766 | 7/1997 | Scheele et al. | 435/912 |
| 5,800,980 | 9/1998 | Perron et al. | 435/5 |
| 5,827,733 | 10/1998 | Lee et al. | 435/325 |
| 5,962,316 | 10/1999 | Beach et al. | 435/325 |

FOREIGN PATENT DOCUMENTS

| | | | |
|---|---|---|---|
| 0173494 | 3/1986 | European Pat. Off. . | |
| 0239400 | 9/1987 | European Pat. Off. . | |
| 2177096B | 5/1989 | United Kingdom . | |
| WO 92/06193 | 4/1992 | WIPO . | |
| 9421681 | 9/1994 | WIPO . | |
| WO 94/21681 | 9/1994 | WIPO | C07K 13/00 |
| 9833887 | 8/1998 | WIPO . | |
| 9906559 | 2/1999 | WIPO . | |
| 9924618 | 5/1999 | WIPO . | |

OTHER PUBLICATIONS

Charlier et al., (1995), The mh gene causing double–muscling . . . , Mammalian Genome 6: 788–792.
Chirgwin et al., (1979). Isolation of biologically active ribonucleic acid . . . , Biochemistry 18:5294–5299.
Cornelis et al., (1992). Identification of a CA repeat at the TCRA locus . . . , Genomics 13:820–825.
Cottingham et al., (1993). Faster sequential genetic linkage computations, Am. J. Hum. Genet. 53:252–263.
Dunner et al., (1997). Towards interbreed IBD fine maping . . . , Mammalian Genomine, in press.
Fisher et al., (1996). Genetic mapping of COL3A1 to bovine chromosome 2. Mammalian Genome 8: 76–77.
Georges et al., (1995). Mapping quantitative trait loci controlling milk . . . , Genetics 139: 907–920.
Hanset et al., (1985). On the genetic determinism of . . . , I. Experimental data. Génét. Sél. Evol. 17: 359–368.
Hanset et al., (1985). On the genetic determinism of . . . , II. Population data. Génét. Sél. Evol. 17: 369–386.
Hanset, R. (1991). The major gene of muscular . . . , Owen, Axford, eds. C.A.B. International, pp. 467–478.

Hudson et al., (1995). Science 270:1945–1954 with supp. data from Whitehead Institute/MIT Center for Genome Research, Human Genetic Mapping Project, data release 11.9 (May 1997).
Hunter et al., (1996). Toward the Construction of Integrated . . . , Genome Research 6:290–299.
Huse et al., (1989). Science 246, 1275–1281.
Kappes et al., (1997). A Second–General Linkage . . . , Genome Research 7:235–249.
Kennett, R. (1979). Cell fusion. Methods Enzymol. 58, 345–359.
Kohler and Milstein, (1975). Nature 256, 459–497.
Lathrop et al., (1984). Easy calculations of lodscores . . . , American Journal of Human Genetics 36:460–465.
Lenstra et al., (1993). Short interspersed nuclear element (SINE) . . . , Animal Genetics 24:33–39.
Libert et al., (1993). Construction of a bovine genomic library of large . . . , Genomics 18:270–276.
Lyons et al., (1996). Comparative Anchor tagged Sequences . . . , Nature Genetics 15:47–56.
McPherron et al., (1996). The transforming growth . . . , In Growth Factors and Cytokines in Health and Disease, vol. 1B, pp. 357–393. JAI press Inc.
McPherron et al., (1997). Regulation of skeletal muscle . . . , Nature 387:83–90.
Ménissier, F. (1982). Present state of knowledge . . . , Current Topics in Veterinary Medicine and Animal Science, vol. 16: Muscle hypertrophy of . . . , pp. 387–428. Eds. King and Ménissier (Martinus Nijhoff).
McCafferty et al., (1990). Nature 348, 552–554.
Mirski et al., (1989). Antigens associated with multidrug resistance in . . . , Cancer Res. 49, 5719–5724.
Morrison et al., (1985). Proc. Natl. Acad. Sci. USA 81, 6851.
O'Brien et al., (1993). Anchored reference loci for comparative genome . . . , Nature Genetics 3:103–112.
Pell et al., (1997). In: Milk Composition, Production and Biotechnology, Ed. Welch et al., Chapter 19.

(List continued on next page.)

*Primary Examiner*—Jeffrey Fredman
*Attorney, Agent, or Firm*—John C. Hunt

[57] ABSTRACT

A gene (cDNA) encoding a bovine myostatin protein. The nucleic acid coding sequence is identified as SEQ ID NO:1 and the protein sequence is identified as SEQ ID NO:2. A mutant gene (SEQ ID NO:3) in which the coding sequence lacks an 11-base pair consecutive sequence (SEQ ID NO:11) of the sequence encoding bovine protein having myostatin activity has been sequenced. It has been shown that cattle of the Belgian Blue breed homozygous for the mutant gene lacking myostatin activity are double-muscled. A method for determining the presence of muscular hyperplasia in a mammal is described. The method includes obtaining a sample of material containing DNA from the mammal and ascertaining whether a sequence of the DNA encoding (a) a protein having biological activity of myostatin, is present, and whether a sequence of the DNA encoding (b) an allelic protein lacking the activity of (a), is present. The absence of (a) and the presence of (b) indicates the presence of muscular hyperplasia in the mammal.

45 Claims, 3 Drawing Sheets

OTHER PUBLICATIONS

Sambrook et al., (1989). Molecular Cloning: A Laboratory Manual. Cold Spring Harbor Lab Press, Cold Spring Harbor, New York.

Solinas–Toldo et al., (1995). Comparative genome map of man and cattle. Genomics 27:489–496.

Staerz & Bevan (1986a). Proc. Natl. Acad. Sci. (USA) 83, 1453.

Staerz & Bevan (1986b). Immunology Today 7, 241.

Stewart et al., (1996). Reduction of Expression of the multidrug . . . , Biochem. Pharmacol. 51, 461–469.

Takeda et al., (1985). Nature 314, 452.

Teng et al., (1982) Meth. Enzymol. 92. 3–16.

Walter et al., (1994). A method for constructing . . . , Nature Genetics 7:22–28.

Ward et al., (1989). Nature 341. 544–546.

McPherron et al., (1997). Double muscling in cattle due to mutations . . . , PNAS 94: 12457–12461.

McKnight, S.L., (1997) Commentary. Gatekeepers of organ growth. PNAS 94: 12249–12250.

Kambadur et al., (1997). Mutations in myostatin (GDF8) in double–muscled . . . , Genome Research 7: 910–916.

Grobet et al., (1997). A deletion in the bovine myostatin gene causes . . . , Nature Genetics 17:71–74.

Grobet et al., (1998). Molecular definition of an allelic series . . . , Mammalian Genome 9:210–213.

Dickman, S., (Sep. 26, 1977). Gene Mutation Provides More Meat . . . , Agricultural Genetics, Science, vol. 277, 1922–1923.

Georges et al., (1997). Positional Candidate Cloning . . . , Presented at the 6th World Congress on Genetics Applied to Animal Production, Armidale, Australia, Jan. 16, 1998.

Hanset, R. (1986). Double–muscling in cattle. In Exploiting New Technologies in Animal Breeding: Genetic Developments. C. Smith, J. King and J. McKay, Eds. Oxford University Press, pp. 71–80.

Hanset, et al., (1982). Studies on the 7th rib in double muscled . . . , In Current Topics in Veterinary Medicine and Animal Science, vol. 16: Muscle Hypertrophy of . . . , pp. 341–349. Eds. King and Mènissier (Martinus Nijhoff).

Hanset, et al., (1987). Relationships between growth rate, carcass, . . . , Génét. Sél. Evol. 19, 225–248.

Bishop et al., (1994). A genetic linkage map for cattle. Genetics 136, 619–639.

Barendse et al,. (1994). A genetic linkage map of the bovine genome. Nature Genet. 6, 227–235.

Collins, F. S. (1995). Positional cloning moves from perditional to traditional. Nature Genet. 9, 347–350.

Georges, M. and Anderson, L. (1996). Livestock Genomics comes of age. Genome Research 6:907–921.

McPherron, et al., "Regulation of skeletal muscle mass in mice by a new TGF–beta superfamily member." Nature, vol. 387, May 1, 1997, pp. 83–90.

Charlier et al., "The mh gene causing double–muscling in cattle maps to the bovine chromosome 2." Mammalian Genome, vol. 6, No. 11, 1995, pp. 788–792.

Grobet et al., "Molecular definitiion of an allelic series of mutations disrupting the myostatin function and causing double–muscling in cattle." Mammalian Genome, vol. 9, No. 3, Mar. 1998, pp. 210–213.

Grobet et al., "A deletion in the bovine myostatin gene causes the double–muscled phenotyp in cattle." Nature Genetics, vol. 17, No. 1, Sep. 1997, pp. 71–74.

McPherron et al., "Double muscling in cattle due to mutations in the myostatin gene." Proc. Natl. Acad. Sci. USA, vol. 94, No. 23, Nov. 11, 1997, pp. 12457–12461.

Kambadur et al., "Mutations in myostatin (GDF8) in double––muscled Belgian Blue and Piedmontese cattle." Genome Research, vol. 7, No. 9, Sep. 1997, pp. 910–916.

Smith et al., "Myostatin maps to the interval containing the bovine mh locus." Mammalian Genome, vol. 8, No. 10, Oct. 1997, pp. 742–744.

Dickman, "Gene mutations provides more meat on the hoof." Science, vol. 277, No. 5334, Sep. 26, 1997, pp. 1922–1923.

Westhusin, "For mighty mice to mighty cows." Nature Genetics, vol. 17, No. 1, Sep. 1997, pp. 71–74.

Georges et al., "Livestock genomics comes of age." Genome Research, vol. 6, 1996, pp. 907–921.

Kappes et al., "A second–generation linkage map of the bovine genome." Genome Research, vol. 7, 1997, pp. 235–249.

Sonstegard et al. "Comparative mapping of human chromosome 2 identifies segments of conserved synteny near the bovine mh locus." Mammalian Genome, vol. 8, 1997, pp. 751–755.

Pirottin et al., "High–resolution human–bovine comparative mapping based on a closed YAC contig spanning the bovine mh locus." Mammalian Genome, vol. 10, 1999, pp. 289–293.

Nezer et al., "An imprinted QTL with major effect on muscle mass and fat deposition maps to the IGF2 locus in pigs." Nat. Genet., vol. 21, 1999, pp. 155–156.

McPherron & Lee, "The transforming growth factor beta superfamily in growth factors and cytokines." in Health and Disease vol. 1B. Eds Leroith & Bondy. (1996) JAI Press Inc.

Fujii et al., "Identification of a mutation in porcine ryanodine receptor associated with malignant hyperthermia." Science, vol. 253, 1991, pp. 448–451.

```
  1
  MMQKLQMVYY IYLFMLIAAG PVDLNEGSER EENVEKEGLC NACAWRQNTR YSRIEAIKIQ ILSKLRLETA   70
  ~~~~~~~~~~ ~~~~~~~~~~ ~~DLNENSEQ KENVEKEGLC NACLWRENTT SSRLEAIKIQ ILSKLRLETA
  ~~~~~~~~~~ ~~~~~~~~~~ PVDLNENSEQ KENVEKEGLC NACLWRENTT SSRLEAIKIQ ILSKLRLETA 71                                100
  PNISKDAIRQ LLPRAPPLRE LIDQYDVQRD
  PNISKDAIRQ LLPKAPPLLE LIDQFDVQRD
  PNISKDAIRQ LLPKAPPLLE LIDQFDVQRD 101                                                       150
  DSSDGSLEDD DYHATTETII TMPTESDFLM QADGKPKCCF FKFSSKIQYN KVVKAQLWIY LRPVKTPTTV
  ASSDGSLEDD DYHARTETVI TMPTESDLLT QVEGKPKCCF FKFSSKIQYN KLVKAQLWIY LRPVKTPATV
  ASSDGSLEDD DYHARTETVI TMPTESDLLT QVEGKPKCCF FKFSSKIQYN KLVKAQLWIY LRPVKTPATV 171                     200
  FVQILRLIKP MKDGTRYTGI RSLKLDMSPG
  FVQILRLIKP MKDGTRYTGI RSLKLDMNPG
  FVQILRLIKP MKDGTRYTGI RSLKLDMNPG 201                                                       250                           270
  TGIWQSIDVK TVLQNWLKQP ESNLGIEIKA LDENGHDLAV TFPGPGEDGL NPFLEVKVTD TPK<u>RSRR</u>DFG
  TGIWQSIDVK TVLQNWLKQP ESNLGIEIKA LDENGHDLAV TFPEPGEDGL TPFLEVKVTD TPK<u>RSRR</u>DFG
  TGIWQSIDVK TVLQNWLKQP ESNLGIEIKA LDENGHDLAV TFPEPGEDGL TPFLEVKVTD TPK<u>RSRR</u>DFG 271                                300
  LD <u>C</u>DEHSTES R<u>CC</u>RYPLTVD FEAFGWDWII
  LD <u>C</u>DEHSTES R<u>CC</u>RYPLTVD FEAFGWDWII
  LD <u>C</u>DRISMLS  LPSNCGF*

301                                                       350
  APKRYKANY<u>C</u> SGE<u>C</u>EFVFLQ KYPHTHLVHQ ANPRGSAGP <u>C</u> <u>C</u>TPTKMSPIN MLYFNGKEQI IYGKIPAMVV DR
                                                                                        376
  APKRYKANY<u>C</u> SGE<u>C</u>EFVFLQ KYPHTHLVHQ ANPRGSAGP <u>C</u> <u>C</u>TPTKMSPIN MLYFNGEGQI IYGKIPAMVV DR <u>CGC</u>S*
                                                                                        <u>CGC</u>S*
```

FIG. 2B

DOUBLE-MUSCLING IN MAMMALS

FIELD OF THE INVENTION

This invention relates to factors affecting muscle development in mammals, especially livestock. In particular, this invention relates to the cloning of the myostatin gene, a member of the TGF-β superfamily, its involvement in muscular hyperplasia in livestock, and a method for determining myostatin genotypes.

DESCRIPTION OF THE RELATED ART

The TGF-β superfamily consists of a group of multifunctional polypeptides which control a wide range of differentiation processes in many mammalian cell types. GDF-8 is a member of the TGF-β superfamily. All members of this superfamily share a common structure including a short peptide signal for secretion and an N-terminal peptide fragment that is separated from the bioactive carboxy-terminal fragment by proteolytic cleavage at a highly conserved proteolytic cleavage site. The bioactive carboxy-terminal domain is characterized by cysteine residues at highly conserved positions which are involved in intra- and intermolecular disulfide bridges. The functional molecules are covalently linked (via a S—S bond) dimers of the carboxy-terminal domain (Masterson et al., 1996).

Recently, it was reported that mice deficient in the gene coding for GDF-8 were characterized by a generalized muscular hyperplasia (McPherron et al, 1997). The GDF-8 deficient mice were produced by gene targeting using homologous recombination in embryonic stem cells, a method referred to as "gene knock-out". The murine generalized muscular hyperplasia appeared to be very similar in its expression to the muscular hyperplasia characterizing "double-muscled" cattle. This observation raised the intriguing possibility that the bovine gene coding for GDF-8 (i.e. the bovine evolutionary homologue of the mouse GDF-8 gene) is involved in the bovine double-muscling phenotype. It also raised the possibility that the human gene coding for GDF-8 (i.e. the human evolutionary homologue of the mouse GDF-8 gene) is involved in regulating muscular development in humans, specifically skeletal muscle genesis. Isolation of the human GDF-8 gene may have therapeutic uses/applications in the treatment of musculodegenerative diseases through upgrading or downgrading the expression of GDF-8.

The occurrence of animals characterized by a distinct generalized muscular hypertrophy, commonly known as "double-muscled" animals, has been reported in several cattle breeds around the world. The first documented description of double-muscled cattle dates back as early as 1807 (Culley, 1807). One of the breeds in which this characteristic has been most thoroughly analyzed is the Belgian Blue Cattle Breed ("Belgian Blue Breed"). This is one of the only breeds where the double-muscled trait has been systematically selected for, and where the double-muscled phenotype is virtually fixed. A comparison of double-muscled and conventional animals within the Belgian Blue Breed, showed an increase in muscle mass by 20% on average, while all other organs were reduced in size (Hanset, 1986 and 1991). The muscular hypertrophy was shown to be an histological hyperplasia affecting primarily superficial muscles, accompanied by a 50% reduction in total lipid content and a reduction in connective tissue fraction as measured by hydroxyproline content (Hanset et al., 1982). Double-muscled animals were shown to have a reduced feed intake with improved feed conversion ratio (Hanset et al., 1987). An important economic benefit of double-muscled animals, in contrast to conventional animals, is the substantial increase in selling price and net income for the farmer (Hanset et al., 1987).

One of the most thorough series of studies on double-muscling is that of Hanset and colleagues in the Belgian Blue Breed. Objective criteria of muscular development, such as dressing-out percentage, lean and fat percentage, plasma and red cell creatine and creatinine concentrations, were measured on nearly 150 randomly selected animals raised in standardized conditions. These studies clearly revealed abnormal, bimodal distributions of the double-muscled phenotype and objectively confirmed the visual classification traditionally performed by breeders on double-muscled and conventional animals. The phenotypic distribution was resolved using a maximum likelihood procedure into two component normal populations with a common variance which revealed mean differences of three to four standard deviations depending on the trait. This suggested the presence of an allele having a major effect on muscular development with a population frequency close to 50% (Hanset and Michaux, 1985b). The most convincing evidence in favour of such an allele, however, came from experimental crosses involving double-muscled Belgian Blue sires and Holstein Friesian dairy cows (the latter animals having very poor muscular development). While F1 offspring showed a phenotypic distribution very similar to their Holstein Friesian dams, backcrossing these F1's to double-muscled sires produced a bimodal BC generation, clearly pointing towards the Mendelian segregation of a recessive "mh" (muscular hypertrophy) allele (Hanset and Michaux., 1985a).

The same kind of experimental crosses were subsequently used to perform a whole genome scan using a microsatellite based marker map. To perform the linkage analysis, animals were classified as double-muscled or conventional. Very significant Logarithm of the Odds scores (lodscores) were obtained on chromosome 2(>17), and multi point linkage analysis positioned the mh locus at the centromeric end of this chromosome, at [2]centimorgan from the nearest microsatellite marker: TGLA44. The corresponding chromosomal region accounted for all the variance of the trait assumed to be fully penetrant in this experiment (Charlier et al., 1995).

In humans genes coding for some forms of muscular abnormalities have been isolated, e.g. muscular dystrophy. The present invention provides for the gene which regulates the development of skeletal muscle only, as opposed to other types of muscle, e.g. smooth or cardiac muscle. The present invention may provide an understanding of the role of the GDF-8 gene or its receptor in the regrowth of skeletal muscle in humans which only undergo a hyperplasic response.

SUMMARY OF THE INVENTION

The present inventors are the first identify and sequence a gene (cDNA) encoding a bovine myostatin protein. The nucleic acid coding sequence is identified as SEQ ID NO:1 and the protein sequence is identified as SEQ ID NO:2. A mutant gene (SEQ ID NO:3) in which the coding sequence lacks an 11-base pair consecutive sequence (SEQ ID NO:11) of the sequence encoding bovine protein having myostatin activity has been sequenced. It has been shown that cattle of the Belgian Blue breed homozygous for the mutant gene lacking myostatin activity are double-muscled.

In one aspect, the present invention thus provides a method for determining the presence of muscular hyperplasia in a mammal. The method includes obtaining a sample of material containing DNA from the mammal and ascertaining whether a sequence of the DNA encoding (a) a protein having biological activity of myostatin, is present, and whether a sequence of the DNA encoding (b) an allelic protein lacking the activity of (a), is present. The absence of (a) and the presence of (b) indicates the presence of muscular hyperplasia in the mammal.

Of course, the mutation responsible for the lack of activity can be a naturally occurring mutation, as is the case for the Belgian Blue breed deletion shown here.

The mammal can be a human, bovine, etc.

There are several methods known for determining whether a particular nucleotide sequence is present in a sample. A common method is the polymerase chain reaction. A preferred aspect of the invention thus includes a step in which ascertaining whether a sequence of the DNA encoding (a) is present, and whether a sequence of the DNA encoding (b) is present includes amplifying the DNA in the presence of primers based on a nucleotide sequence encoding a protein having biological activity of myostatin.

A primer of the present invention, used in PCR for example, is a nucleic acid molecule sufficiently complementary to the coding sequence on which it is based and of sufficient length to selectively hybridize to the corresponding portion of a nucleic acid molecule intended to be amplified and to prime synthesis thereof under in vitro conditions commonly used in PCR. Likewise, a probe of the present invention, is a molecule, for example a nucleic acid molecule of sufficient length and sufficiently complementary to the nucleic acid molecule of interest, which selectively binds under high or low stringency conditions with the nucleic acid sequence of interest for detection thereof in the presence of nucleic acid molecules having differing sequences.

In preferred aspects, primers are based on the sequence identified as SEQ ID NO:7.

In another aspect, the invention is a method for determining the presence of muscular hyperplasia in a mammal which includes obtaining a sample of material containing mRNA from the mammal. Such method includes ascertaining whether a sequence of the mRNA encoding (A) a protein having biological activity of myostatin, is present, and whether a sequence of the mRNA encoding (B) a protein at least partially encoded by a truncated nucleotide sequence corresponding to substantially the sequence of the mRNA and lacking the activity of (A), is present. The absence of (A) and the presence of (B) indicates the presence of muscular hyperplasia in the mammal.

The mRNA encoding (A) and the truncated sequence can correspond to alleles of DNA of the mammal.

Again, if an amplification method such as PCR is used in ascertaining whether a sequence of the mRNA encoding (A) is present, and whether a sequence of the mRNA encoding (B) is present, the method includes amplifying the mRNA in the presence of a pair of primers complementary to a nucleotide sequence encoding a protein having biological activity of myostatin. Each such primer can contain a nucleotide sequence substantially complementary, for example, to the sequence identified as SEQ ID NO:7. The truncated sequence can contain at least 50 consecutive nucleotides substantially corresponding to 50 consecutive nucleotides of SEQ ID NO:7, for example.

In another aspect, the invention is a method for determining the presence of muscular hyperplasia in a mammal which includes obtaining a tissue sample of containing mRNA of the mammal and ascertaining whether an mRNA encoding a mutant type myostatin protein lacking biological activity of myostatin is present. The presence of such an mRNA encoding a mutant type myostatin protein indicates the presence of muscular hyperplasia in the mammal.

In another aspect, the invention thus provides a method for determining the presence of muscular hyperplasia in a bovine animal. The method includes obtaining a sample of material containing DNA from the animal and ascertaining whether DNA having a nucleotide sequence encoding a protein having biological activity of myostatin is present. The absence of DNA having such a nucleotide sequence indicates the presence of muscular hyperplasia in the animal. Ascertaining whether DNA having a nucleotide sequence encoding a protein having biological activity of myostatin can include amplifying the DNA in the presence of primers based on a nucleotide sequence encoding a protein having biological activity of myostatin.

In particular, the method can be carried out using a sample from an animal in which such a bovine animal not displaying muscular hyperplasia is known to have a nucleotide sequence which is capable of hybridizing with a nucleic acid molecule having the sequence identified as SEQ ID NO:1 under stringent hybridization conditions.

It is possible that ascertaining whether DNA having a nucleotide sequence encoding a protein having biological activity of myostatin is present includes amplifying the DNA in the presence of primers based on a nucleotide sequence encoding the N-terminal and the C-terminal, respectively, of the protein having biological activity of myostatin.

Primers, say first and second primers, can be based on first and second nucleotide sequences encoding spaced apart regions of the protein, wherein the regions flank a mutation known to naturally occur and which when present in both alleles of a such an animal results in muscular hyperplasia.

It can also be that DNA of such an animal not displaying muscular hyperplasia contains a nucleotide sequence which hybridizes under stringent conditions with a nucleotide sequence encoding a protein having a sequence identified as SEQ ID NO:2 and the coding sequence of DNA of a such an animal displaying muscular hyperplasia is known to contain an 11-base pair deletion beginning at base pair no. 821 of the coding sequence, and said first primer is selected to be upstrean of the codon encoding glutamic acid no. 275 and the second primer is selected to be downstream of the codon encoding aspartic acid no. 274.

Also, a DNA of such an animal not displaying muscular hyperplasia might contain a nucleotide sequence which hybridizes under stringent conditions with a nucleotide sequence encoding a protein having a sequence identified as SEQ ID NO:2. The coding sequence of DNA of such an animal displaying muscular hyperplasia might be known to contain an 11-base pair deletion beginning at base pair no. 821. A primer can be selected to span the nucleotide sequence including base pair nos. 820 and 821 of the DNA sequence containing the deletion.

The animal can be of the Belgian Blue breed.

In a particular aspect, ascertaining whether DNA having a nucleotide sequence encoding a protein having biological activity of myostatin is present includes amplifying the DNA in the presence of a primer containing at least a portion of a mutation known to naturally occur and which when present in both alleles of a said animal results in muscular hyperplasia.

In another aspect, the invention is a method for determining the presence of muscular hyperplasia in a bovine animal which includes obtaining a sample of the animal containing mRNA and ascertaining whether an mRNA encoding a protein having biological activity of myostatin is present in the sample. The absence of said mRNA indicates the presence of muscular hyperplasia in the animal.

A sample containing mRNA can be muscle tissue, particularly, skeletal muscle tissue.

In a particular aspect, the invention is a method for determining the presence of double muscling in a bovine animal, involving obtaining a sample of material containing DNA from the animal and ascertaining whether the DNA contains the nucleotide sequence identified as SEQ ID NO:11 in which the absence of the sequence indicates double muscling in the animal.

In a particular aspect, the animal is of the Belgian Blue breed.

In another aspect, the invention is a method for determining the myostatin genotype of a mammal, as may be desirable to know for breeding purposes. The method includes obtaining a sample of material containing nucleic acid of the mammal, wherein the nucleic acid is uncontaminated by heterologous nucleic acid; ascertaining whether the sample contains a (i) nucleic acid molecule encoding a protein having biological activity of myostatin; and ascertaining whether the sample contains an (ii) allelic nucleic acid molecule encoding a protein lacking biological activity of myostatin. The mammal can be bovine.

In another aspect, the subject is human and (i) includes a nucleic acid sequence substantially homologous (in the sense of identity) with the sequence identified as SEQ ID NO:7.

The invention includes a purified protein having biological activity of myostatin, and having an amino acid sequence identified as SEQ ID NO:2, or a conservatively substituted variant thereof The invention includes a purified bovine protein having biological activity of myostatin or a purified human protein having biological activity of myostatin.

The invention includes an isolated nucleic acid molecule encoding a foregoing protein. Particularly, the invention includes an isolated nucleic acid molecule comprising a DNA molecule having the nucleotide sequence identified as SEQ ID NO:1 or SEQ ID NO:3 or SEQ ID NO:7 or which varies from the sequence due to the degeneracy of the genetic code, or a nucleic acid strand capable of hybridizing with at least one said nucleic acid molecule under stringent hybridization conditions.

The invention includes isolated mRNA transcribed from DNA having a sequence which corresponds to a nucleic acid molecule of the invention.

The invention includes isolated DNA in a recombinant cloning vector and a microbial cell containing and expressing heterologous DNA of the invention.

The invention includes a transfected cell line which expresses a protein of the invention.

The invention includes a process for producing a protein of the invention, including preparing a DNA fragment including a nucleotide sequence which encodes the protein; incorporating the DNA fragment into an expression vector to obtain a recombinant DNA molecule which includes the DNA fragment and is capable of undergoing replication; transforming a host cell with the recombinant DNA molecule to produce a transformant which can express the protein; culturing the transformant to produce the protein; and recovering the protein from resulting cultured mixture.

The invention includes a method of inhibiting myostatin in a mammal in need thereof, comprising administering an effective amount of an antibody to myostatin to the mammal.

The invention includes of inhibiting myostatin in a mammal in need thereof, by raising an autoantibody to the myostatin the in the mammal. Raising the autoantibody can include administering a protein having myostatin activity to the mammal.

The invention includes a method of inhibiting production of myostatin in a mammal in need thereof, including administering to the mammal an effective amount of an antisense nucleic acid or oligonucleotide substantially complementary to at least a portion of the sequence identified as SEQ ID NO:1 or SEQ ID NO:5, or SEQ ID NO:7. The portion can be at least 5 nucleotide bases in length or longer. The mammal can be a bovine and the sequence can be that identified as SEQ ID NO:1.

The invention includes a method of inhibiting production of myostatin in a mammal in need thereof, including administering to the mammal an effective amount of an antibody to the myostatin.

The invention includes a probe containing a nucleic acid molecule sufficiently complementary with a sequence identified as SEQ ID NO:1, or its complement, so as to bind thereto under stringent conditions. The probe can be a sequence which is between about 8 and about 1195 nucleotides in length.

The invention includes a primer composition useful for detection of the presence of DNA encoding myostatin in cattle. The composition can include a nucleic acid primer substantially complementary to a nucleic acid sequence encoding a bovine myostatin. The nucleic acid sequence can be that identified as SEQ ID NO:1.

The invention includes a method for identifying a nucleotide sequence of a mutant gene encoding a myostatin protein of a mammal displaying muscular hyperplasia. The method includes obtaining a sample of material containing DNA from the mammal and probing the sample using a nucleic acid probe based on a nucleotide sequence of a known gene encoding myostatin in order to identify nucleotide sequence of the mutant gene. In a particular approach, the probe is based on a nucleotide sequence identified as SEQ ID NO:1, SEQ ID NO:5 or SEQ ID NO:7. Preferably, the probe is at least 8 nucleic acids in length. The step of probing the sample can include exposing the DNA to the probe under hybridizing conditions and further comprising isolating hybridized nucleic acid molecules. The method can further include the step of sequencing isolated DNA. The method can include the step of isolating and sequencing a cDNA or mRNA encoding the complete mutant myostatin protein. The method can include a step of isolating and sequencing a functional wild type myostatin from the mammal not displaying muscular hyperplasia.

The method can include comparing the complete coding sequence of the complete mutant myostatin protein with, if the coding sequence for a functional wild type myostatin from such a mammal is previously known, (1) the known sequence, or if the coding sequence for a functional wild type myostatin from such a mammal is previously unknown, (2) the sequence determined according to claim 37 or claim 40, to determine the location of any mutation in the mutant gene.

The invention includes a primer composition useful for the detection of a nucleotide sequence encoding a myostatin containing a first nucleic acid molecule based on a nucleotide sequence located upstream of a mutation determined according to a method of the invention and a second nucleic acid molecule based on a nucleotide sequence located downstream of the mutation.

A probe of the invention can include a nucleic acid molecule based on a nucleotide sequence spanning a mutation determined according to the invention.

The invention includes an antibody to a protein encoded by a nucleotide sequence identified as SEQ ID NO:1, SEQ ID NO:3 or SEQ ID NO:7, or other protein of the present invention.

The invention includes a transgenic bovine having a genome lacking a gene encoding a protein having biological activity of myostatin; a transgenic mouse having a genome containing a gene encoding a human protein having biological activity of myostatin or containing a gene encoding a bovine protein having biological activity of myostatin; a transgenic bovine having a gene encoding a bovine protein having biological activity of myostatin and heterologous nucleotide sequence antisense to the gene. The transgenic bovine can include a gene encoding a nucleic acid sequence having ribozyme activity and in transcriptional association with the nucleotide sequence antisense to the gene.

BRIEF DESCRIPTION OF THE DRAWINGS

In describing particular aspects of the invention, reference is made to the accompanying drawings, in which:

FIG. 2(b) shows the amino-acid sequence of the murine (top row), bovine normal (middle row) and bovine nt821del (11) (bottom row) allele. The putative site of proteolytic processing is boxed, while the nine conserved cysteines in the carboxy-terminal region are underlined. The differences between the normal and nt821del(11) bovine allele are indicated by the double underlining.

DETAILED DESCRIPTION OF THE PREFERRED EMBODIMENTS

Figure 1:
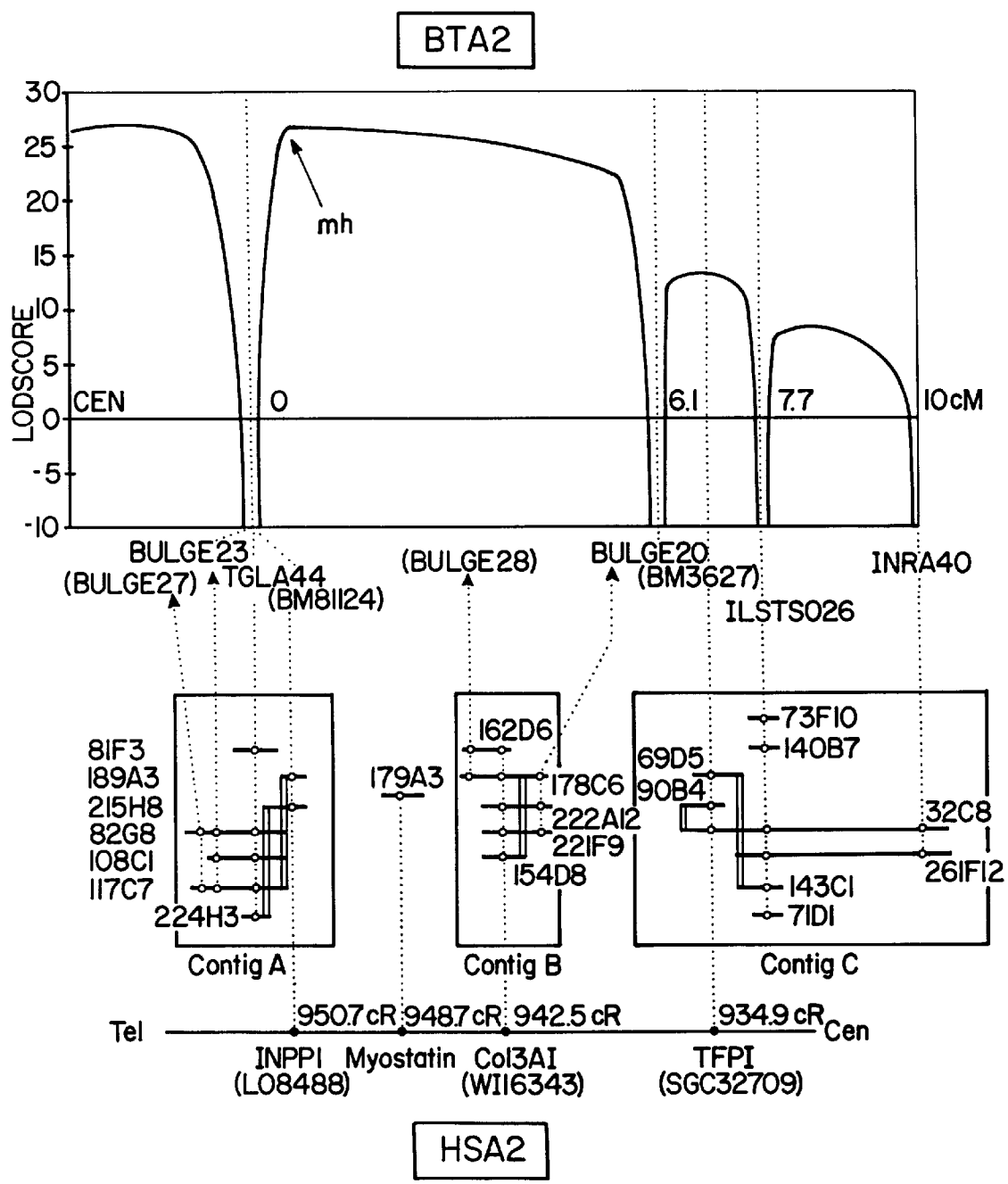
FIG. 1 is a schematic summary of genetic, physical and comparative mapping information around the bovine mh locus. A multi-point lodscore curve obtained for the mh locus with respect to the microsatellite marker map is shown. Markers that were not informative in the pedigree used are shown between brackets; their map position is inferred from published mapping data. Markers and the YACs from which they were isolated are connected by arrows. The RH-map of the relevant section of human HSA2 is shown, with the relative position in cR of the ESTs used. Stippled lines connect microsatellite and Type I markers with their respective positive YACs. YACs showing cross-hybridizing SINE-PCR products are connected by the red boxes.

The method used for isolating genes which cause specific phenotypes is known as positional candidate cloning. It involves: (i) the chromosomal localization of the gene which causes the specific phenotype using genetic markers in a linkage analysis; and (ii) the identification of the gene which causes the specific phenotype amongst the "candidate" genes known to be located in the corresponding region. Most of the time these candidate genes are selected from available mapping information in humans and mice.

The tools required to perform the initial localization (step (i) above) are microsatellite marker maps, which are available for livestock species and are found in the public domain (Bishop et al., 1994; Barendse et al., 1994; Georges et al., 1995; and Kappes, 1997). The tools required for the positional candidate cloning, particularly the YAC libraries, (step (ii) above) are partially available from the public domain. Genomic libraries with large inserts constructed with Yeast Artificial Chromosomes ("YAC") are available in the public domain for most livestock species including cattle. When cross-referencing the human and mice map, it is necessary to identify the positional candidate, which is available at low resolution but needs to be refined in every specific instance to obtain the appropriate level of high resolution. A number of original strategies are described herein to achieve this latter objective. For general principles of positional candidate cloning, see Collins, 1995 and Georges and Andersson, 1996.

In order to allow for cross-referencing between the bovine and human gene map as part of the positional candidate cloning approach, HSA2q31–32 (map of the long arm of human chromosome 2, cytogenetic bands q31–32) and BTA2q12–22 (map of the arm of bovine chromosome 2, cytogenetic bands q12–22) were integrated on the basis of coincidence bovine YAC's as described below.

Using a previously described experimental [(normal×double-muscled)×double-muscled] backcross population comprising 108 backcross individuals, the mh locus was recently mapped by linkage analysis to the centromeric tip of bovine chromosome 2 (BTA2), at 3.1 centiMorgan proximal from the last marker on the linkage map: TGLA44 (Charlier et al., 1995). It was also known from previous work that pro-α(III) collagen (Col3AI) was located in the same chromosomal region as the mh locus. Indeed, Col3AI has been mapped to BTA2q12–22 by in situ hybridization (Solinas-Toldo et al., 1995), while a Col3AIRFLP marker was shown to be closely linked to TGLA44 (θ=2%)(Fisher et al., 1996). This identifies the region flanking Col3AI on the human map, i.e. HSA2q31–32, as the likely orthologous human chromosome segment. This assumption is compatible with data from Zoo-FISH experiments (Solinas-Toldo et al., 1995) as well as mapping data of Type I markers on somatic cell hybrids (O'Brien et al., 1993), which establish an evolutionary correspondence between segments of HSA2q and BTA2.

In order to refine the correspondence between the HSA2q31–33 and BTA2q12–22 maps, Comparative Anchored Tagged Sequences or CATS, i.e. primer pairs that would amplify a Sequence Tagged Site or STS from the orthologous gene in different species (Lyons et al., 1996), were developed for a series of genes flanking Col3AI on the human map and for which sequence information was available in more than one mammal. In addition to Col3AI, working CATS were obtained for α2(V) collagen (Col5A2), inositol polyphosphate-1 phosphatase (INPP1), tissue factor pathway inhibitor precursor (TFPI), titin (TTN), n-chimaerin (CHN), glutamate decarboxylase 67 (GAD1), Cytotoxic T-lymphocyte-associated protein 4 (CTLA4) and T-cell membrane glycoprotein CD28 (CD28). The corresponding primer sequences are given in Table 2.

These CATS were used to screen a 6-genome equivalent bovine YAC library by PCR using a three-dimensional pooling strategy as described by Libert et al., 1994. The same YAC library was also screened with all microsatellite markers available for proximal BTA2, i.e. TGLA44, BM81124, BM3627, ILSTS026, INRA40 and TGLA431 (Kappes et al., 1996).

Potential overlap between the YACs obtained with this panel of STS's was explored on the basis of common STS content, as well as cross-hybridization between SINE-PCR product from individual YACs. From this analysis, three independent YAC contigs emerged in the region of interest: (i) contig A containing microsatellites TGLA44, BM81124 and Type I marker INPP1; (ii) contig B containing Col3AI and Col5A2; and (iii) contig C containing microsatellite markers BM3627, ILSTS026 and INRA40, and Type I marker TFPI.

None of the available microsatellites mapped to contig B, therefore this cluster of YACs could not be positioned in cattle with respect to the two other contigs. Available mapping information in the human, however, allowed prediction of contig B's position between contigs A and C. To test this hypothesis, two new microsatellite markers were isolated from contig B, BULGE20 and BULGE28. BULGE20 proved to be polymorphic, allowing for genotyping of the experimental backcross population.

In addition, to increase the informativeness of the markers available for contig A, two new microsatellite markers were developed from this contig: BULGE23 and BULGE27. BULGE23 proved to be polymorphic and was used to type the same pedigree material.

All resulting genotypes were used to construct a linkage map using the ILINK program (Lathrop and Lalouel, 1984). The following most likely order and sex-averaged recombination rates between adjacent markers was obtained: [TGLA44-(0%)-BULG23]-(6,1%)-BULG20-(1,6%)-ILSTS026-(2.3%)-INRA40-(7,1 %)-TGLA43 1. The position of BULGE20 between TGLA44 and ILSTS026 confirmed the anticipated order of the three contigs. FIG. 1 summarizes the resulting mapping information.

A multi point linkage analysis was undertaken using LINKMAP, to position the mh locus with respect to the new marker map. Linkage analysis was performed under a simple recessive model, assuming full penetrance for mh/mh individuals and zero penetrance for the two other genotypes. The LOD score curve shown in FIG. 1 was obtained, placing the mh locus in the TGLA44-BULGE20 interval with an associated maximum LOD score of 26.4. Three backcross individuals were shown to recombine with the BULGE20 and distal markers, but not with TGLA44 and BULGE23, therefore placing the mh locus proximal from this marker. One individual, was shown to recombine with TGLA44 and BULGE23, but not with the more distal markers, therefore positioning the mh locus distal from TGLA44 and BULGE23. Given the relative position of these microsatellite markers with respect to INPP1 and Col3AI as deduced from the integration of the human and bovine map, these results indicated that the mh gene is likely located in a chromosome segment bounded by INPP1 and Col3AI Recently, McPherron et al. (1997) demonstrated that mice homozygous for a knock-out deletion of GDF-8 or myostatin, were characterized by a generalized increase in skeletal muscle mass. Using the published 2676 bp murine myostatin cDNA sequence (GenBank accession number U84005), a Tentative Human Consensus (THC) cluster in the Unigene database was identified which represented three cDNA clones (221299, 300367, 308202) and six EST (Expressed Sequence Tag) sequences (H92027, H92028, N80248, N95327, W07375, W24782). The corresponding THC covered 1296 bp of the human myostatin gene, showing an homology of 78.1% with the murine sequence when averaged over the entire sequence, and 91.1% when considering only the translated parts of the human and murine genes (566 bp). This THC therefore very likely corresponds to the human orthologue of the murine myostatin gene.

Primers (5'-GGCCCAACTATGGATATATTTG-3' (SEQ ID NO:9) and 5'-GGTCCTGGGAAGGTTACAGCA-3' (SEQ ID NO:10)) were thus prepared to amplify a 272 bp fragment from the second exon of human myostatin and used to genotype the whole-genome Genebridge-4 radiation hybrid panel (Walter et al., 1994). The RHMapper program (Slonim et al., unpublished) was used to position the myostatin gene with respect to the Whitehead/MIT framework radiation hybrid map, placing it at position 948.7 cR of the HSA2 map with an associated lodscore >3. Closer examination of the myostatin segregation vector and its confrontation with the vectors from all markers located in that region (Data Release 11.9, May 1997) showed it to be identical to EST SGC38239 placed on the Whitehead/MIT radiation hybrid map (Hudson et al., 1995) at position 946.8 cR of HSA2. This places the human myostatin gene on the RH-map in the interval between Col3AI (EST WI16343—942.5 cR) and INPP1 (EST L08488—950.2 to 951.2 cR)(FIG. 1). Myostatin therefore appeared as a very strong positional candidate for the mh gene.

To test the potential involvement of myostatin in the determinism of double-muscling in cattle, primer pairs were designed based on the available mouse and human myostatin sequence, with the objective to amplify the entire coding sequence from bovine cDNA using PCR (Polymerase Chain Reaction). Whenever possible, primers were therefore positioned in portions of the myostatin sequence showing 100% homology between mouse and human. Two primer pairs were identified that amplified what was predicted to represent 98.4% of the bovine coding sequence plus 74 bp of 3' untranslated sequence, in two overlapping DNA fragments, respectively 660 (primers GDF8.19—GDF8.12) and 724 bp (primers GDF8.11—GDF8.21) long. The expected DNA products were successfully amplified from cDNA generated from skeletal muscle of both a normal (homozygous +/+) (SEQ ID NO:1) and a double-muscled (homozygous mh/mh) (SEQ ID NO:3) animal, and cycle-sequenced on both strands.

The nucleotide sequence corresponding to the normal allele presented 88.9% identity with the mouse myostatin sequence (SEQ ID NO:5) over a 1067 bp overlap, and contained the expected open reading frame encoding a protein (SEQ ID NO:2) showing 92.9% identity in a 354 amino-acid overlap with mouse myostatin (SEQ ID NO:6). As expected for a member of the TGFβ superfamily, the bovine myostatin gene is characterized by a proteolytic processing site thought to mediate cleavage of the bioactive carboxy-terminal domain from the longer N-terminal fragment, and by nine cysteine residues separated by a characteristic spacing and suspected to be involved in intra- and inter-molecular disulfide bridges (McPherron and Lee, 1996).

Figure 2A:
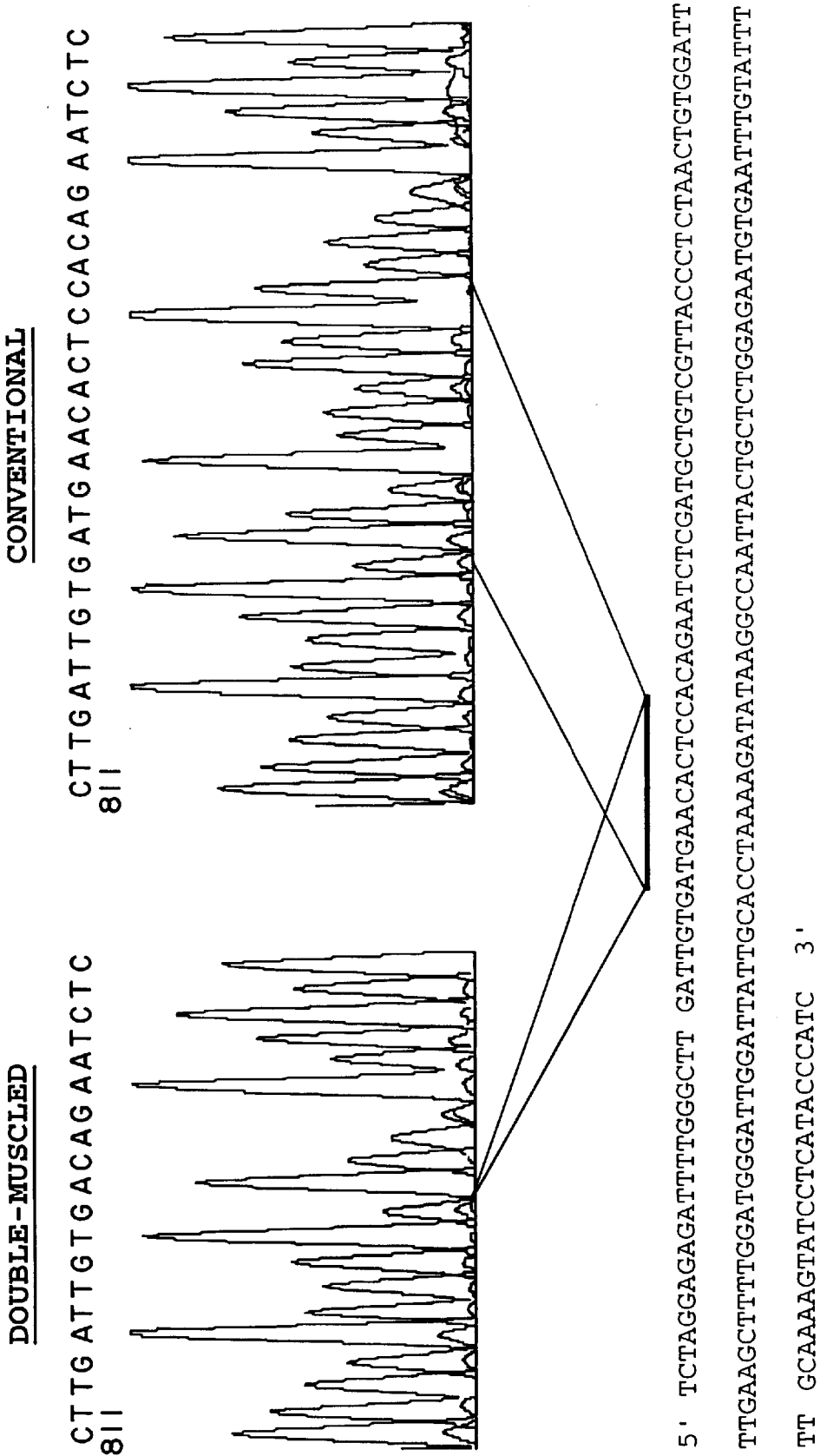
FIG. 2(a) shows electropherograms obtained by cycle-sequencing the myostatin cDNA sequence from a double-muscled and a conventional animal, showing the nt821del (11) deletion in the double-muscled animal. The primers used to amplify the fragment encompassing the deletion from genomic DNA are spaced apart from the remaining nucleotides.

The nucleotide sequence obtained from the mh allele was identical to the normal allele over its entire length, except for an 11 bp deletion involving nucleotides 821 to 831 (counting from the initiation codon). This frame shifting deletion, occurring after the first cysteine residue of the carboxy-terminal domain, drastically disrupts the downstream amino-acid sequence and reveals a premature stop-codon after 13 amino acids, see FIG. 2. This mutation disrupts the bioactive part of the molecule and is therefore very likely to be the cause of the recessive double-muscling phenotype. Following conventional nomenclature, this mutation will be referred to as nt821(de11).

To further strengthen the assumption of the causality of this mutation, primer pairs flanking the deletion (FIG. 2) were prepared and the corresponding DNA segment from all animals from the experimental backcross population amplified. PCR was performed in the presence of dCTP$^{32}$ in order to radioactively label the amplification product. Amplification products were separated on denaturing polyacrylamide gels and detected by autoradiography. A 188 bp product would be expected for the normal allele and a 177 bp product for the nt821(del11) allele. Correlation between phenotype and genotype was matched for the entire pedigree. All ten BBCB double-muscled sires were found to be homozygous for the nt821(del11) mutation, all 41 F1 females were heterozygous, while 53 double-muscled offspring were homozygous for the mutation, the remaining 55 conventional animals were heterozygous.

To examine the distribution of the nt821(del11) mutation in different conventional and double-muscled breeds, a cohort of 25 normal individuals was genotyped representing two dairy breeds (Holstein-Friesian, Red-and-White) and a cohort of 52 double-muscled animals representing four breeds (BBCB, Asturiana, Maine-Anjou and Piémontese). The results are summarized in Table 1. All dairy animals were homozygous normal except for one Red-and-White bull shown to be heterozygous. The occurrence of a small fraction of individuals carrying the mutation in dairy cattle is not unexpected as the phenotype is occasionally described in this breed. In BBCB and Asturiana, all double-muscled animals were homozygous for the nt821(del11) deletion, pointing towards allelic homogeneity in these two breeds, for which locus homogeneity had been demonstrated before (Dunner et al., 1997). Double-muscled Maine-Anjou and Piémontese animals were homozygous "normal", i.e. they did not show the nt821(del11) deletion. As the role of the mh locus in double-muscling has been clearly demonstrated by marker assisted segregation analysis in Maine-Anjou, this points towards the likely existence of allelic heterogeneity amongst double-muscled breeds. Evidence for the role of the mh locus in double muscling in Piémontese is not yet available, but the role of the nt821(del11) mutation can be excluded as the only cause of the double-muscling phenotype in this breed.

TABLE 1

| Breed | Pheno-type | Genotype +/+ | +/nt821(del11) | nt821(del11)/nt821(del11) |
|---|---|---|---|---|
| Belgian Blue | DM | | | 29 |
| Asturiana | DM | | | 10 |
| Piémontese | DM | 8 | | |
| Maine-Anjou | DM | 4 | | |
| Holstein-Friesian | Normal | 13 | | |
| Red-and-White | Normal | 12 | 1 | |

TABLE 2

CATS

| | | | | |
|---|---|---|---|---|
| INPP1 | UP: 5' CAGCAAAGTCTTAATGGTAACAAGC 3' | DN: 5' GGGTCACTGAAGAAAACGTCCTG 3' |
| COL3A1 | UP: 5' CCCCATATTATGGAGATGAACCG 3' | DN: 5' AGTTCAGGATGGCAGAATTTCAG 3' |
| COL5A2 | UP: 5' GCAAACTGGGYGGRAGCAAGACC 3' | DN: 5' TTSTTCCTGGGCTTTTATTGAGAC 3' |
| TFPI | UP: 5' AAGCCWGATTTCTGCTTYTTGGAAG 3' | DN: 5'TGCCMAGGCAHCCRCCRTACTTGAA 3' |
| TTN | UP: 5' GGTCGTCCTACACCAGAAG 3' | DN: 5' GGTGACATTGTCAAGAACAAG 3' |
| CHN | UP: 5' TCTCMAAAGTCGTCTGTGACAATC 3' | DN: 5' TGYTCRTTTTCTTTCAGAGTTGC 3' |
| GAD1 | UP: 5' RCTGGTCCTCTTCACCTCAGAAC 3' | DN: 5' ACATTGTCVGTTCCAAAGCCAAG 3' |
| CTLA4 | UP: 5' AGGTYCGGGTGACDGTGCTKC 3' | DN: 5' TGGRTACATGAGYTCCACCTTGC 3' |
| CD28 | UP: 5' AGCTGCARTGTATWCCTACAAYCT 3' | DN: 5' GTYCCRTTGCTCYTCTCRTTGYC 3' |

Microsatellite markers

| | | |
|---|---|---|
| TGLA44 | UP: 5' AACTGTATATTGAGAGCCTACCATG 3' | DN: 5' CACACCTTAGCGACTAAACCACCA 3' |
| BULGE27 | UP: 5' CTACCTAACAGAATGATTTTGTAAG 3' | DN: 5' AGTGTTCTTGCCTAGAGAATCCCAG 3' |
| BULGE23 | UP: 5'ACATTCTCTCACCAATATGACATAC 3' | DN: 5' TAAGTCACCATTACATCCTTAGAAC 3' |
| BM81124 | UP: 5' GCTGTAAGAATCTTCATTAAGCACT 3' | DN: 5' CCTGATACATGCTAAGGTTAAAAAC 3' |
| BULGE28 | UP: 5' AGGCATACATCTGGAGAGAAACTATG 3' | DN: 5' CAGAGGAGCCTAGCAGGCTACCGTC 3' |
| BULGE20 | UP: 5' CAGCAGGTCTGTTGAAGTGTATCAG 3' | DN: 5' AGTGGTAGCATTCACAGGTAGCCAG 3' |
| BM3627 | UP: 5' CAGTCCATGGCACCATAAAG 3' | DN: 5' TCCGTTAGTACTGGCTAATTGC 3' |
| ILSTS026 | UP: 5' CTGAATTGGCTCCAAAGGCC 3' | DN: 5' AAACAGAAGTCCAGGGCTGC 3' |
| INRA40 | UP: 5' TCAGTCTCCAGGAGAGAAAAC 3' | DN: 5' CTCTGCCCTGGGGATGATTG 3' |

Bovine Myosostatin primers

GDF8.19 5' AATGTATGTTTATATTTACCTGTTCATG 3'

TABLE 2-continued

```
GDF8.11  5' ACAGTGTTTGTGCAAATCCTGAGAC 3'

GDF8.12  5' CAATGCCTAAGTTGGATTCAGGTTG 3'

GDF8.25  5' CTTGCTGTAACCTTCCCAGGACCAG 3'

GDF8.15  5' TCCCATCCAAAGGCTTCAAAATC 3'

GDF8.21  5' ATACTCWAGGCCTAYAGCCTGTGGT 3'
```

Reading from left to right and down the table, the sequences given in Table 1 are identified as SEQ ID NO:12 to SEQ ID NO:52, and SEQ ID NO:8, respectively.

EXAMPLE 1

Genetic and Physical Mapping

Integration of the HSA2q31–32 and BTA2q12–22 maps was done by using coincident YAC's and the mh locus was positioned in the interval flanked by Col3AI and INPP1 as follows. Genetic mapping was performed using a previously described (Holstein-Friesian×Belgian Blue)×Belgian Blue experimental backcross population counting 108 informative individuals (Charlier et al., 1995). Microsatellite genotyping was performed according to standard procedures (Georges et al., 1995), using the primer sequences reported in Table 2. Linkage analyses were performed with the MLINK, ILINK and LINKMAP programs of the LINKAGE (version 5.1) and FASTLINK (2.3P version, June 1995) packages (Lathrop & Lalouel, 1984; Cottingham et al., 1993). The YAC library was screened by PCR using a three dimensional pooling scheme as described in Libert et al., 1994. The primer pairs corresponding to the CATS used to screen the library are reported in Table 2. Cross-hybridisation between SINE-PCR products of individual YACs was performed according to Hunter et al. (1996), using primers reported in Lenstra et al. (1993). Microsatellites were isolated from YACs according to Cornelis et al. (1992).

EXAMPLE 2

Mapping of the Human Myostatin Gene on the Genebridge-4-Panel

DNA from the Genebridge-4 panel (Walter et al., 1994) was purchased from Research Genetics (Huntsville, Ala.), and genotyped by PCR using standard procedures and the following human myostatin primer pair (5'-GGCCCAACTATGGATATATTTG-3' and 5'-GGTCCTGGGAAGGTTACAGCA-3'). Mapping was performed via the WWW server of the Whitehead Institute/MIT Center for Genome Research using their RH-mapper program (Slonim, D.; Stein, L.; Kruglyak, L.; Lander, E., unpublished) to position the markers with respect to the framework map. Segregation vectors of the query markers were compared with the vectors from all markers in the region of interest in the complete Data Release 11.9 (May 1997) to obtain a more precise position. This positions myostatin in the INPP1-Col3AI on the human map with LOD score superior to 3.

EXAMPLE 3

RT-PCR

To clone the bovine myostatin orthologue a strategy based on RT-PCR amplification from skeletal muscle cDNA was chosen. Total RNA was extracted from skeletal muscle (*Triceps brachialis*) according to Chirgwin et al. (1979). RT-PCR was performed using the Gene-Amp RNA PCR Kit (Perkin-Elmer) and the primers reported in Table 2. The PCR products were purified using QiaQuick PCR Purification kit (Qiagen) and sequenced using Dye terminator Cycle Sequencing Ready Reaction (Perkin elmer) and an ABI373 automatic sequencer, using the primers reported in Table 2.

EXAMPLE 4

Diagnosis of the nt821(del11) deletion

To diagnose the nt821 (del 11) the following primer sequences were designed flanking the nt821(del11) deletion: 5'-TCTAGGAGAGATTTTGGGCTT-3' (SEQ ID NO:53) and 5-GATGGGTATGAGGATACTTTTGC-3' (SEQ ID NO:52). These primers amplify a 188 bp fragments from normal individuals and a 177 bp fragment from double-muscled individuals. Heterozygous individuals show the two amplification products. These amplification products can be detected using a variety of methods. In this example the PCR product was labelled by incorporation of $dCTP^{32}$, separated on a denaturing acrylamide gel and revealed by autoradiography. Other approaches that could be used to distinguish the three different genotypes are known to those skilled in the art and would include separation in agarose gels and visualization with ethidium bromide, direct sequencing, TaqMan assays, hybridization with allele specific oligonucleotides, reverse dot-blot, RFLP analysis and several others. The specificity of the test is linked to the detected mutation and not to the primers used in the detection method. That means that other primers can easily be designed based on said bovine myostatin sequence that would fulfill the same requirements.

Monoclonal antibodies (Mab's) specific for myostatin are useful. In the case of the bovine protein having the amino acid sequence identified as SEQ ID NO:2, for example, antibodies can be used for diagnostic purposes such as for determining myostatin protein levels in muscle tissue. To produce these antibodies, purified myostatin is prepared. The myostatin can be produced in bacterial cells as a fusion protein with glutathione-S-transferase using the vector pGEX2 (Pharmacia). This permits purification of the fusion protein by GSH affinity chromatography. In another approach, myostatin is expressed as a fusion protein with the bacterial maltose binding domain. The fusion protein is thus recovered from bacterial extracts by passing the extract over an amylose resin column followed by elution of the fusion protein with maltose. For this fusion construct, the vector pMalC2, commercially available from New England Biolabs, can be used. The preparation of a second fusion protein is also useful in the preliminary screening of MAb's.

The generation of hybridomas expressing monoclonal antibodies recognizing myostatin protein is carried out as follows: BALB/c mice are injected intraperitoneally with protein/adjuvant three times at one-month intervals, followed by a final injection into the tail vein shortly prior to cell fusion. Spleen cells are harvested and fused with NS-1 myeloma cells (American Type Culture Collection, Rockville, Md.) using polyethylene glycol 4000 according to standard protocols (Kennett, 1979; Mirski, 1989). The cell fusion process is carried out as described in more detail below.

The fused cells are plated into 96-well plates with peritoneal exudate cells and irradiated spleen cells from BALB/Cc mice as feeder layers and selection with hypoxanthine, aminopterin, and thymidine (HAT medium) is performed.

An ELISA assay is used as an initial screening procedure. 1–10 µg of purified myostatin (cleaved from the fusion protein) in PBS is used to coat individual wells, and 50–100 µl per well of hybridoma supernatants is incubated. Horseradish peroxidase-conjugated anti-mouse antibodies are used for the calorimetric assay.

Positive hybridomas are cloned by limiting-dilution and grown to large-scale for freezing and antibody production. Various positive hybridomas are selected for usefulness in western blotting and immunohistochemistry, as well as for cross reactivity with myostatin proteins from different species, for example the mouse and human proteins.

Alternatively, active immunization by the generation of an endogenous antibody by direct exposure of the host animal to small amounts of antigen can be carried out. Active immunization involves the injection of minute quantities of antigen (g) which probably will not induce a physiological response and will be degraded rapidly. Antigen will only need to be administered as prime and boost immunizations in much the same manner as techniques used to confer disease resistance (Pell et al., 1997).

Antisense nucleic acids or oligonucleotides (RNA or preferably DNA) can be used to inhibit myostatin production. Antisense oligonucleotides, typically 15 to 20 bases long, bind to the sense mRNA or pre mRNA region coding for the protein of interest, which can inhibit translation of the bound mRNA to protein. The cDNA sequence encoding myostatin can thus be used to design a series of oligonucleotides which together span a large portion, or even the entire cDNA sequence. These oligonucleotides can be tested to determine which provides the greatest inhibitory effect on the expression of the protein (Stewart, 1996). The most suitable mRNA target sites include 5'- and 3'-untranslated regions as well as the initiation codon. Other regions might be found to be more or less effective. Alternatively, an antisense nucleic acid or oligonucleotide may bind to myostatin coding or regulatory sequences.

Rather than reducing myostatin activity by inhibiting myostatin gene expression at the nucleic acid level, activity of the myostatin protein may be directly inhibited by binding to an agent, such as, for example, a suitable small molecule or a monoclonal antibody.

It will of course be understood, without the intention of being limited thereby, that a variety of substitutions of amino acids is possible while preserving the structure responsible for myostatin activity of the proteins disclosed herein. Conservative substitutions are described in the patent literature, as for example, in U.S. Pat. No. 5,264,558. It is thus expected, for example, that interchange among non-polar aliphatic neutral amino acids, glycine, alanine, proline, valine and isoleucine, would be possible. Likewise, substitutions among the polar aliphatic neutral amino acids, serine, threonine, methionine, asparagine and glutamine could possibly be made. Substitutions among the charged acidic amino acids, aspartic acid and glutamic acid, could probably be made, as could substitutions among the charged basic amino acids, lysine and arginine. Substitutions among the aromatic amino acids, including phenylalanine, histidine, tryptophan and tyrosine would also likely be possible. These sorts of substitutions and interchanges are well known to those skilled in the art. Other substitutions might well be possible. Of course, it would also be expected that the greater the percentage of homology, i.e., sequence similarity, of a variant protein with a naturally occurring protein, the greater the retention of metabolic activity. Of course, as protein variants having the activity of myostatin as described herein are intended to be within the scope of this invention, so are nucleic acids encoding such variants.

A further advantage may be obtained through chimeric forms of the protein, as known in the art. A DNA sequence encoding the entire protein, or a portion of the protein, could thus be linked, for example, with a sequence coding for the C-terminal portion of E. coli β-galactosidase to produce a fusion protein. An expression system for human respiratory syncytial virus glycoproteins F and G is described in U.S. Pat. No. 5,288,630 issued Feb. 22, 1994 and references cited therein, for example.

A recombinant expression vector of the invention can be a plasmid, as described above. The recombinant expression vector of the invention further can be a virus, or portion thereof, which allows for expression of a nucleic acid introduced into the viral nucleic acid. For example, replication defective retroviruses, adenoviruses and adeno-associated viruses can be used.

The recombinant expression vectors of the invention can be used to make a transformant host cell including the recombinant expression vector. The term "transformant host cell" is intended to include prokaryotic and eukaryotic cells which have been transformed or transfected with a recombinant expression vector of the invention. The terms "transformed with", "transfected with", "transformation" and "transfection" are intended to encompass introduction of nucleic acid (e.g. a vector) into a cell by one of many possible techniques known in the art. Prokaryotic cells can be transformed with nucleic acid by, for example, electroporation or calcium-chloride mediated transformation. Nucleic acid can be introduced into mammalian cells via conventional techniques such as calcium phosphate or calcium chloride coprecipitation, DEAE-dextran-mediated transfection, lipofection, electroporation or microinjection. Suitable methods for transforming and transfecting host cells are known (Sambrook, 1989).

The number of host cells transformed with a recombinant expression vector of the invention by techniques such as those described above will depend upon the type of recombinant expression vector used and the type of transformation technique used. Plasmid vectors introduced into mammalian cells are integrated into host cell DNA at only a low frequency. In order to identify these integrants, a gene that contains a selectable marker (e.g. resistance to antibiotics) is generally introduced into the host cells along with the gene of interest. Preferred selectable markers include those which confer resistance to certain drugs, such as G418 and hygromycin. Selectable markers can be introduced on a separate plasmid from the nucleic acid of interest or, preferably, are introduced on the same plasmid. Host cells transformed with one or more recombinant expression vectors containing a nucleic acid of the invention and a gene for a selectable marker can be identified by selecting for cells using the selectable marker. For example, if the selectable marker encodes a gene conferring neomycin resistance (such as pRc/CMV), transformant cells can be selected with G418. Cells that have incorporated the selectable marker gene will survive, while the other cells die.

Nucleic acids which encode myostatin proteins having can be used to generate transgenic animals. A transgenic animal (e.g., a mouse) is an animal having cells that contain a transgene, which transgene is introduced into the animal or an ancestor of the animal at a prenatal, e.g., an embryonic stage. A transgene is a DNA which is integrated into the genome of a cell from which a transgenic animal develops. In one embodiment, a bovine cDNA, comprising the nucleotide sequence shown in SEQ ID NO:1, or an appropriate variant or subsequence thereof, can be used to generate transgenic animals that contain cells which express bovine myostatin. Likewise, variants such as mutant genes (e.g. SEQ ID NO:3) can be used to generate transgenic animals. This could equally well be done with the human myostatin protein and variants thereof "Knock out" animals, as described above, can also be generated. Methods for generating transgenic animals, particularly animals such as mice, have become conventional in the art are described, for example, in U.S. Pat. Nos. 4,736,866 and 4,870,009. In a preferred embodiment, plasmids containing recombinant molecules of the invention are microinjected into mouse embryos. In particular, the plasmids are microinjected into the male pronuclei of fertilized one-cell mouse eggs; the injected eggs are transferred to pseudo-pregnant foster females; and, the eggs in the foster females are allowed to develop to term. (Hogan, 1986). Alternatively, an embryonal stem cell line can be transfected with an expression vector comprising nucleic acid encoding a myostatin protein, and cells containing the nucleic acid can be used to form aggregation chimeras with embryos from a suitable recipient mouse strain. The chimeric embryos can then be implanted into a suitable pseudopregnant female mouse of the appropriate strain and the embryo brought to term. Progeny harboring the transfected DNA in their germ cells can be used to breed uniformly transgenic mice.

Such animals could be used to determine whether a sequence related to an intact myostatin gene retains biological activity of myostatin. Thus, for example, mice in which the murine myostatin gene has been knocked out and containing the nucleic acid sequence identified as SEQ ID NO:1 could be generated along with animals containing the nucleic acid sequence identified as SEQ ID NO:3. The animals could be examined for display of muscular hyperplasia, especially in comparison with knockout mice, which are known to display such. In this way it can be shown that the protein encoded by SEQ ID NO:3 lacks myostatin activity within the context of this invention while the protein encoded by the nucleic acid sequence identified as SEQ ID NO:1 possesses biological activity of myostatin.

In such experiments, muscle cells would be particularly targeted for myostatin (and variants) transgene incorporation by use of tissue specific enhancers operatively linked to the encoding gene. For example, promoters and/or enhancers which direct expression of a gene to which they are operatively linked preferentially in muscle cells can be used to create a transgenic animal which expresses a myostatin protein preferentially in muscle tissue. Transgenic animals that include a copy of a myostatin transgene introduced into the germ line of the animal at an embryonic stage can also be used to examine the effect of increased myostatin expression in various tissues.

The pattern and extent of expression of a recombinant molecule of the invention in a transgenic mouse is facilitated by fusing a reporter gene to the recombinant molecule such that both genes are co-transcribed to form a polycistronic mRNA. The reporter gene can be introduced into the recombinant molecule using conventional methods such as those described in Sambrook et al., (Sambrook, 1989). Efficient expression of both cistrons of the polycistronic mRNA encoding the protein of the invention and the reporter protein can be achieved by inclusion of a known internal translational initiation sequence such as that present in poliovirus mRNA. The reporter gene should be under the control of the regulatory sequence of the recombinant molecule of the invention and the pattern and extent of expression of the gene encoding a protein of the invention can accordingly be determined by assaying for the phenotype of the reporter gene. Preferably the reporter gene codes for a phenotype not displayed by the host cell and the phenotype can be assayed quantitatively. Examples of suitable reporter genes include IacZ (β-galactosidase), neo (neomycin phosphotransferase), CAT (chloramphenicol acetyltransferase) dhfr (dihydrofolate reductase), aphIV (hygromycin phosphotransferase), lux (luciferase), uidA (β-glucuronidase). Preferably, the reporter gene is lacZ which codes for β-galactosidase. β-galactosidase can be assayed using the lactose analogue X-gal (5-bromo-4-chloro-3-indolyl-b-D-galactopyranoside) which is broken down by P-galactosidase to a product that is blue in color (Old).

The present invention includes knocking out wild type myostatin in mammals, in order to obtain the desired effect(s) thereof This is particularly true in cattle raised for beef production. It may well prove advantageous to substitute a defective gene (e.g. SEQ ID NO:3 or it genomic analogue) rather than delete the entire sequence of DNA encoding for a protein having myostatin activity. A method of producing a transgenic bovine or transgenic bovine embryo is described in U.S. Pat. No. 5,633,076, issued May 27, 1997, for example.

The transgenic animals of the invention can be used to investigate the molecular basis of myostatin action. For example, it is expected that myostatin mutants in which one or more of the conserved cysteine residues has been deleted would have diminished activity in relation to a wild type myostatin protein in which all such residues are retained. Further, deletion of proteolytic cleavage site would likely result in a mutant lacking biological activity of myostatin.

Transgenesis can be used to inactivate myostatin activity. This could be achieved using either conventional transgenesis, i.e. by injection in fertilized oocytes, or by gene targeting methods using totipotent cell lines such as ES (embryonic stem cells) which can then be injected in oocytes and participate in the development of the resulting organisms or whose nucleus can be transferred into unfertilized oocytes, nucleus transfer or cloning.

Using conventional transgenesis a gene coding for a myostatin antisense is injected, for example, by inverting the orientation of the myostain gene in front of its natural promoter and enhancer sequences. This is followed by injection of a gene coding for an anti-myostain ribozyme, i.e. an RNA that would specifically bind to endogenous myostain mRNA and destroy it via its "ribozyme" activity.

Also, through gene targeting, a conventional knock-out animal can be generated, specific mutations by gene replacement can be engineered. It is possible to inactivate the myostain gene at a specific developmental time, such as after birth to avoid calving difficulties. This could be achieved using the Cre-1ox P systems in which 1.ox P sides are engineered around the myostain gene by homologous recombination (gene targeting), and mating these animals with transgenic animals having a Cre transgene (coding for the Cre recombinase existing DNA flanked by J oxP sides) under the dependence of a skeletal muscle specific promoter only active after birth. This is done to obtain individuals that would inactivate their myostain gene after birth. There are also gene targeting systems that allow genes to be turned on and off by feeding an animal with, for example, an antibiotic. In such an instance, one engineers an operator between the promoter of the gene and the gene itself This operator is the target of a repressor which when binding inactivates the gene (for example, the lac operon in *E. coli*). The repressor is brought into the cell using conventional transgenesis, for example, by injection of the gene coding for the repressor.

Transgenic animals of the invention can also be used to test substances for the ability to prevent, slow or enhance myostatin action. A transgenic animal can be treated with the substance in parallel with an untreated control transgenic animal.

The antisense nucleic acids and oligonucleotides of the invention are useful for inhibiting expression of nucleic acids (e.g. mRNAs) encoding proteins having myostatin activity.

The isolated nucleic acids and antisense nucleic acids of the invention can be used to construct recombinant expression vectors as described previously. These recombinant expression vectors are then useful for making transformant host cells containing the recombinant expression vectors, for expressing protein encoded by the nucleic acids of the invention, and for isolating proteins of the invention as described previously. The isolated nucleic acids and antisense nucleic acids of the invention can also be used to construct transgenic and knockout animals as described previously.

The isolated proteins of the invention are useful for making antibodies reactive against proteins having myostatin activity, as described previously. Alternatively, the antibodies of the invention can be used to isolate a protein of the invention by standard immunoaffinity techniques. Furthermore, the antibodies of the invention, including bispecific antibodies are useful for diagnostic purposes.

Molecules which bind to a protein comprising an amino acid sequence shown in SEQ ID NO:2 can also be used in a method for killing a cell which expresses the protein, wherein the cell takes up the molecule, if for some reason this were desirable. Destruction of such cells can be accomplished by labeling the molecule with a substance having toxic or therapeutic activity. The term "substance having toxic or therapeutic activity" as used herein is intended to include molecules whose action can destroy a cell, such as a radioactive isotope, a toxin (e.g. diphtheria toxin or ricin), or a chemotherapeutic drug, as well as cells whose action can destroy a cell, such as a cytotoxic cell. The molecule binding to the myostatin can be directly coupled to a substance having a toxic or therapeutic activity or may be indirectly linked to the substance. In one example, the toxicity of the molecule taken up by the cell is activated by myostatin protein.

The invention also provides a diagnostic kit for identifying cells comprising a molecule which binds to a protein comprising an amino acid sequence shown in SEQ ID NO:2, for example, for incubation with a sample of tumor cells; means for detecting the molecule bound to the protein, unreacted protein or unbound molecule; means for determining the amount of protein in the sample; and means for comparing the amount of protein in the sample with a standard. Preferably, the molecule is a monoclonal antibody. In some embodiments of the invention, the detectability of the molecule which binds to myostatin is activated by said binding (e.g., change in fluorescence spectrum, loss of radioisotopic label). The diagnostic kit can also contain an instruction manual for use of the kit.

The invention further provides a diagnostic kit for identifying cells comprising a nucleotide probe complementary to the sequence, or an oligonucleotide fragment thereof, shown in SEQ ID NO:1, for example, for hybridization with mRNA from a sample of cells, e.g., muscle cells; means for detecting the nucleotide probe bound to mRNA in the sample with a standard. In a particular aspect, the invention is a probe having a nucleic acid molecule sufficiently complementary with a sequence identified as SEQ ID NO:1, or its complement, so as to bind thereto under stringent conditions. "Stringent hybridization conditions" takes on its common meaning to a person skilled in the art here. Appropriate stringency conditions which promote nucleic acid hybridization, for example, 6× sodium chloride/sodium citrate (SSC) at about 45° C. are known to those skilled in the art. The following examples are found in Current Protocols in Molecular Biology, John Wiley & Sons, New York (1989), 6.3.1–6.3.6: For 50 ml of a first suitable hybridization solution, mix together 24 ml formamide, 12 ml 20× SSC, 0.5 ml 2 M Tris-HCl pH 7.6, 0.5 ml 100× Denhardt's solution, 2.5 ml deionized $H_2O$, 10 ml 50% dextran sulfate, and 0.5 ml 10% SDS. A second suitable hybridization solution can be 1% crystalline BSA (fraction V), 1 mM EDTA, 0.5 M $Na_2HPO_4$ pH 7.2, 7% SDS. The salt concentration in the wash step can be selected from a low stringency of about 2× SSC at 50° C. to a high stringency of about 0.2× SSC at 50° C. Both of these wash solutions may contain 0.1% SDS. In addition, the temperature in the wash step can be increased from low stringency conditions at room temperature, about 22° C., to high stringency conditions, at about 65° C. The cited reference gives more detail, but appropriate wash stringency depends on degree of homology and length of probe. If homology is 100%, a high temperature (65° C. to 75° C.) may be used. If homology is low, lower wash temperatures must be used. However, if the probe is very short (<100 bp), lower temperatures must be used even with 100% homology. In general, one starts washing at low temperatures (37° C. to 40° C.), and raises the temperature by 3–5° C. intervals until background is low enough not to be a major factor in autoradiography. The diagnostic kit can also contain an instruction manual for use of the kit.

The invention provides purified proteins having biological activity of myostatin. The terms "isolated" and "purified" each refer to a protein substantially free of cellular material or culture medium when produced by recombinant DNA techniques, or chemical precursors or other chemicals when chemically synthesized. In certain preferred embodiments, the protein having biological activity of myostatin comprises an amino acid sequence identified as SEQ ID NO:2. Furthermore, proteins having biological activity of myostatin that are encoded by nucleic acids which hybridize under stringent conditions, as discussed above, to a nucleic acid comprising a nucleotide sequence identified as SEQ ID NO:1 or SEQ ID NO:7 are encompassed by the invention. Proteins of the invention having myostatin activity can be obtained by expression in a suitable host cell using techniques known in the art. Suitable host cells include prokaryotic or eukaryotic organisms or cell lines, for example, yeast, *E. coli*, insect cells and COS 1 cells. The recombinant expression vectors of the invention, described above, can be used to express a protein having myostatinI activity in a host cell in order to isolate the protein. The invention provides a method of preparing an purified protein of the invention comprising introducing into a host cell a recombinant nucleic acid encoding the protein, allowing the protein to be expressed in the host cell and isolating and purifying the protein. Preferably, the recombinant nucleic acid is a recombinant expression vector. Proteins can be isolated from a host cell expressing the protein and purified according to standard procedures of the art, including ammonium sulfate precipitation, column chromatography (e.g. ion exchange, gel filtration, affinity chromatography, etc.), electrophoresis, and ultimately, crystallization (see generally, "Enzyme Purification and Related Techniques", *Methods in Enzymology*, 22, 233–577 (1971)).

Alternatively, the protein or parts thereof can be prepared by chemical synthesis using techniques well known in the chemistry of proteins such as solid phase synthesis (Merrifield, 1964), or synthesis in homogeneous solution (Houbenwcyl, 1987).

The protein of the invention, or portions thereof, can be used to prepare antibodies specific for the proteins. Antibodies can be prepared which bind to a distinct epitope in an unconserved region of a particular protein. An unconserved region of the protein is one which does not have substantial sequence homology to other proteins, for example other members of the myostatin family or other members of the TGFβ superfamily. Conventional methods can be used to prepare the antibodies. For example, by using a peptide of a myostatin protein, polyclonal antisera or monoclonal antibodies can be made using standard methods. A mammal, (e.g. a mouse, hamster, or rabbit) can be immunized with an immunogenic form of the peptide which elicits an antibody response in the mammal. Techniques for conferring immunogenicity on a peptide include conjugation to carriers or other techniques well known in the art. For example, the peptide can be administered in the presence of adjuvant. The progress of immunization can be monitored by detection of antibody titers in plasma or serum. Standard ELISA or other immunoassay can be used to assess the levels of antibodies. Following immunization, antisera can be obtained and, if desired, polyclonal antibodies isolated from the sera.

To produce monoclonal antibodies, antibody producing cells (lymphocytes) can be harvested from an immunized animal and fused with myeloma cells by standard somatic cell fusion procedures, thus immortalizing these cells and yielding hybridoma cells. Such techniques are well known in the art. For example, the hybridoma technique originally developed by Kohler and Milstein (Kohler, 1975) as well as other techniques such as the human B-cell hybridoma technique (Kozbor, 1983), the EBV-hybridoma technique to produce human monoclonal antibodies (Cole, 1985), and screening of combinatorial antibody libraries (Huse, 1989). Hybridoma cells can be screened immunochemically for production of antibodies specifically reactive with the peptide, and monoclonal antibodies isolated.

The term antibody as used herein is intended to include fragments thereof which are also specifically reactive with a protein having the biological activity of myostatin, or a peptide fragment thereof. Antibodies can be fragmented using conventional techniques and the fragments screened for utility in the same manner as described above for whole antibodies. For example, F(ab')$_2$ fragments can be generated by treating antibody with pepsin. The resulting F(ab')$_2$ fragment can be treated to reduce disulfide bridges to produce Fab' fragments.

It is also known in the art to make chimeric antibody molecules with human constant regions. See, for example, Morrison et al., Takeda et al., Cabilly et al., Boss et al., Tanaguchi et al., Teng et al. (Morrison, 1985; Takeda, 1985; Cabilly; Boss; Tanaguchi; Teng, 1982), European Patent Publication 0173494, United Kingdom Patent GB 2177096B, PCT Publication WO92/06193 and EP 0239400. It is expected that such chimeric antibodies would be less immunogenic in a human subject than the corresponding non-chimeric antibody.

Another method of generating specific antibodies, or antibody fragments, reactive against protein having the biological activity of a myostatin protein, or a peptide fragment thereof, is to screen expression libraries encoding immunoglobulin genes, or portions thereof, expressed in bacteria, with peptides produced from the nucleic acid molecules of the present invention. For example, complete Fab fragments, VH regions and FV regions can be expressed in bacteria using phage expression libraries. See for example Ward et al., Huse et al., and McCafferty et al. (Ward, 1989; Huse, 1989; McCafferty, 1990). Screening such libraries with, for example, a myostatin protein can identify immunoglobulin fragments reactive with myostatin. Alternatively, the SCID-hu mouse developed by Genpharm can be used to produce antibodies, or fragments thereof.

The polyclonal, monoclonal or chimeric monoclonal antibodies can be used to detect the proteins of the invention, portions thereof or closely related isoforms in various biological materials, for example they can be used in an ELISA, radioimmunoassay or histochemical tests. Thus, the antibodies can be used to quantify the amount of a myostatin protein of the invention, portions thereof or closely related isoforms in a sample in order to determine the role of myostatin proteins in particular cellular events or pathological states. Using methods described hereinbefore, polyclonal, monoclonal antibodies, or chimeric monoclonal antibodies can be raised to nonconserved regions of myostatin and used to distinguish a particular myostatin from other proteins.

The polyclonal or monoclonal antibodies can be coupled to a detectable substance or reporter system. The term "coupled" is used to mean that the detectable substance is physically linked to the antibody. Suitable detectable substances include various enzymes, prosthetic groups, fluorescent materials, luminescent materials and radioactive materials. Examples of suitable enzymes include horseradish peroxidase, alkaline phosphatase, β-galactosidase, and acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride and phycoerythrin; an example of a luminescent material includes luminol; and examples of suitable radioactive material include $^{125}$I; $^{131}$I, $^{35}$S and $^{3}$H. In a preferred embodiment, the reporter system allows quantitation of the amount of protein (antigen) present.

Such an antibody-linked reporter system could be used in a method for determining whether a fluid or tissue sample of a subject contains a deficient amount or an excessive amount of the protein. Given a normal threshold concentration of such a protein for a given type of subject, test kits could thus be developed.

The present invention allows the skilled artisan to prepare bispecific antibodies and tetrameric antibody complexes. Bispecific antibodies can be prepared by forming hybrid hybridomas (Staerz, 1986a &b).

Compositions of the invention are administered to subjects in a biologically compatible form suitable for pharmaceutical administration in vivo. By "biologically compatible from suitable for administration in vivo" is meant a form of the composition to be administered in which any toxic effects are outweighed by the therapeutic effects of the composition. The term "subject" is intended to include living organisms in which a desired therapeutic response can be elicited, e.g. mammals. Examples of subjects include cattle, human, dogs, cats, mice, rats and transgenic species thereof Administration of a therapeutically active amount of the therapeutic compositions of the present invention is defined as an amount effective, at dosages and for periods of time necessary to achieve the desired result. For example, a therapeutically active amount of a compound that inhibits the biological activity of myostatin protein may vary according to factors such as the age, sex, and weight of the individual, as well as target tissue and mode of delivery. Dosage regimes may be adjusted to provide the optimum therapeutic response. For example, several divided doses may be administered daily or the dose may be proportionally reduced as indicated by the exigencies of the therapeutic situation.

Those skilled in the art will know, or be able to ascertain using no more than routine experimentation, many equivalents to the described herein. Such equivalents are described herein. Such equivalents are intended to be encompassed by the following claims.

REFERENCES

Particulars of references cited above are given below. All of the listed references are incorporated herein by reference.

Boss et al., U.S. Pat. No. 4,816,397.

Cabilly et al. U.S. Pat. No. 4,816,567.

Charlier, C.; Coppieters, W.; Farnir, F.; Grobet, L.; Leroy, P.; Michaux, C.; Mni, M.; Schwers, A.; Vanmanshoven, P.; Hanset, R. & Georges, M. (1995) The mh gene causing double-muscling in cattle maps to bovine chromosome 2. Mammalian Genome 6: 788–792.

Chirgwin, J. M.; Przybyla, A. E.; MacDonald, R. J.; Rutter, W. J. (1979) Isolation of biologically active ribonucleic acid from sources enriched in ribonuclease. Biochemistry 18:5294–5299.

Cole et al. (1985). Monoclonal Antibodies in Cancer Therapy. Allen R. Bliss, Inc.

Cornelis, F.; Hashimoto, L.; Loveridge, J.; MacCarthy, A.; Buckle, V.; Julier, C.; Bell, J. (1992). Identification of a CA repeat at the TCRA locus using YACs: a general method for generating highly polymorphic markers at chosen loci. Genomics 13:820–825.

Cottingham, R. W.; Idury, R. M.; Schäffer, A. A. (1993). Faster sequential genetic linkage computations. Am. J. Hum. Genet. 53: 252–263.

Dunner, S.; Charlier, C.; Farnir, F.; Brouwers, B.; Canon, J.; Georges, M. Towards interbreed IBD fine mapping of the mh locus: double-muscling in the Asturiana de los Valles breed involves the same locus as in the Belgian Blue cattle breed. (1997) Mammalian Genome, in press.

Fisher, S. R.; Beever, J. E.; Lewin, H. A. (1996). Genetic mapping of COL3AI to bovine chromosome 2. Mammalian Genome 8:76–77.

Georges, M.; Nielsen, D.; Mackinnon, M.; Mishra, A.; Okimoto, R.; Pasquino, A. T.; Sargeant, L. S.; Sorensen, A.; Steele, M. R.; Zhao, X.; Womack, J. E.; Hoeschele, I. (1995). Mapping quantitative trait loci controlling milk production by exploiting progeny testing. Genetics 139: 907–920.

Hanset, R. and Michaux, C. (1985a). On the genetic determinism of muscular hypertrophy in the Belgian White and Blue cattle breed. I. Experimental data. Génét. Sél. Evol. 17: 359–368.

Hanset, R. and Michaux, C. (1985b). On the genetic determinism of muscular hypertrophy in the Belgian White and Blue cattle breed. II. Population data. Génét. Sél. Evol. 17: 369–386.

Hanset, R. (1991). The major gene of muscular hypetrophy in the belgian Blue Cattle Breed. In *Breeding for Disease Resistance in Farm Animals*, Owen, Axford, eds. C.A.B. International, pp.467–478.

Hogan, B. et al., (1986). A Laboratory Manual, Cold Spring Harbor, N.Y., Cold Spring Harbor Laboratory.

Houbenwcyl, (1987). Methods of Organic Chemistry, ed. E. Wansch. Vol. 15 I and II. Thieme, Stuttgart.

Hudson et al. (1995) Science 270:1945–1954 with supplementary data from the Whitehead Institute/MIT Center for Genome Research, Human Genetic Mapping Project, data release 11.9 (May 1997)

Hunter, K.; Riba, L.; Schalkwyk, L.; Clark, M.; Resenchuk, S.; Beeghly, A.; Su, J.; Tinkov, F.; Lee, P.; Ramu, E.; Lehrach, H. and Housman, D. (1996). Toward the Construction of Integrated Physical and Genetic Maps of the Mouse Genome Using Interspersed Repetitive Sequence PCR (IRS/NPCR) Genomics. Genome Research 6:290–299.

Huse et al., (1989). Science 246, 1275–1281.

Kappes, S. M.; Keele, J. W.; Stone, R. T.; McGraw, R. A.; Sonstegard, T. S.; Smith, T. P. L.; Lopez-Corrales, N. L. and Beattie, C. W. (1997). A Second-Generation Linkage Map of the Bovine Genome. Genome Research 7:235–249.

Kennett, R. (1979). Cell fusion. Methods Enzymol. 58, 345–359.

Kohler and Milstein. (1975). Nature 256, 495–497.

Kozbor et al. (1983). Immunol. Today 4, 72.

Lathrop, M.; Lalouel, J. M. (1984). Easy calculations of lodscores and genetic risk on small computers. American Journal of Human Genetics 36: 460–465.

Lenstra, J. A.; van Boxtel, J. A. F.; Zwaagstra, K. A.; Schwerin, M. (1993). Short interspersed nuclear element (SINE) sequences of the Bovidae. Animal Genetics 24:33–39.

Libert, F.; Lefort, A.; Okimoto, R.; Georges, M. (1993) Construction of a bovine genomic library of large yeast artificial chromosome clones. Genomics 18:270–276.

Lyons, A. L.; Laughlin, T. F.; Copeland, N. G.; Jenkins, N. A.; Womack, J. E.; O'Brien, S. J. (1996). Comparative Anchor tagged Sequences for Integrative mapping of Mammalian Genomes. Nature Genetics 15:47–56.

McPherron, A. C.; Lee, S.-J. (1996). The transforming growth factor β superfamily. In Growth Factors and Cytokines in Health and Disease, Volume 1B, pages 357–393. JAI press Inc.

McPherron, A. C.; Lawler, A. M.; Lee, S.-J. (1997). Regulation of skeletal muscle mass in mice by a new TGFβ superfamily member. Nature 387:83–90.

Ménissier, F. (1982). Present state of knowledge about the genetic determination of muscular hypertrophy or the double muscled trait in cattle. in *Current Topics in Veterinary Medicine and Animal Science, vol. 16: Muscle hypertrophy of genetic origin and its use to improve beef production*, pp. 387–428. Ed. King and Ménissier, Martinus Nijhoff.

Merrifield, (1964]. J. Am. Chem. Assoc. 85, 2149–2154.

McCafferty et al., (1990). Nature 348, 552–554.

Mirski, S. and Cole, S. P. C. (1989). Antigens associated with multidrug resistance in H69AR, a small cell lung cancer cell line. Cancer Res. 49, 5719–5724.

Morrison etal., (1985). Proc. Natl. Acad. Sci. U.S.A. 81, 6851.

O'Brien, S. J.; Womack, J. E.; Lyons, L. A.; Moore, K. J.; Jenkins, N.A.; Copeland, N. G. (1993). Anchored reference loci for comparative genome mapping in mammals. Nature Genetics 3: 103–112.

Old, R. W. and Primrose, S. B., In: Principles of Gene Manipulation. An Introduction to Genetic Engineering, 4th ed. Oxford University Press. 63–66.

Pell, J. M.; Flint, D. J.; (1997). In: Milk Composition, Production and Biotechnology, Ed. Welch et al., Chapter 19.

Sambrook, J., Fritsch E. F. and Maniatis, T. (1989). Molecular Cloning: A Laboratory Manual. Cold Spring Harbor Lab Press, Cold Spring Harbor, New York.

Solinas-Toldo, S.; Lengauer, C; Fries, R. (1995). Comparative genome map of man and cattle. Genomics 27: 489–496.

Staerz & Bevan (1986a). Proc. Natl. Acad. Sci. (U.S.A.) 83, 1453.

Staerz & Bevan (1986b). Immunology Today 7, 241.

Stewart, A. J., Canitrot, Y., Baracchini, E., Dean, N. M., Deeley, R. G., and Cole, S. P. C. (1996). Reduction of Expression of the multidrug resistance protein (MRP) in human tumor cells by antisense phophorothioate oligonucleotides. Biochem. Pharamcol. 51, 461–469.

Takeda et al., (1985). Nature 314,452.

Tanaguchi et al., European Patent Publication EP171496.

Teng, et al. (1982) Meth. Enzymol. 92. 3–16.

Walter, M. A.; Spillett, D. J.; Thomas, P.; Weissenbach, J.; Goodfellow, P. N. (1994). A method for constructing radiation hybrid maps of whole genomes. Nature Genetics 7:22–28.

Ward et al, (1989). Nature 341. 544–546.

What is claimed is:

1. A method for determining the presence of muscular hyperplasia in a bovine animal, the method comprising:
    obtaining a sample of material containing DNA from a said animal; and
    ascertaining whether DNA having a nucleotide sequence encoding a protein having biological activity of myostatin is present by amplifying the DNA in the presence of first and second primers based on first and second nucleotide sequences encoding spaced apart regions of the protein, wherein said regions flank a naturally occurring mutation and which when present in both alleles of a said animal results in said muscular hyperplasia,
wherein the absence of DNA having said nucleotide sequence indicates the presence of muscular hyperplasia in the animal.

2. The method of claim 1 wherein ascertaining whether DNA having a nucleotide sequence encoding a protein having biological activity of myostatin includes amplifying the DNA in the presence of primers based on a nucleotide sequence encoding a protein having biological activity of myostatin.

3. The method of claim 2 wherein DNA of a said bovine animal not displaying muscular hyperplasia has a nucleotide sequence which is capable of hybridizing with a nucleic acid molecule having the sequence identified as SEQ ID NO:1 under stringent hybridization conditions.

4. The method of claim 1, wherein ascertaining whether DNA having a nucleotide sequence encoding a protein having biological activity of myostatin is present includes amplifying the DNA in the presence of primers based on a nucleotide sequence encoding the N-terminal and the C-terminal, respectively, of the protein having biological activity of myostatin.

5. The method of claim 1 wherein a DNA of said animal not displaying muscular hyperplasia contains a nucleotide sequence which hybridizes under stringent conditions with a nucleotide sequence encoding a protein having a sequence identified as SEQ ID NO:2 and said first primer is selected to be upstream of the codon encoding glutamic acid no. 275 and the second primer is selected to be downstream of the codon encoding aspartic acid no. 274.

6. The method of claim 1 wherein a DNA of said animal not displaying muscular hyperplasia contains a nucleotide sequence which hybridizes under stringent conditions with a nucleotide sequence encoding a protein having a sequence identified as SEQ ID NO:2 and the coding sequence of DNA of a said animal displaying muscular hyperplasia is known to contain an 11-base pair deletion beginning at base pair no. 821, and said primer is selected to span the nucleotide sequence including base pair nos. 820 and 821 of the DNA sequence containing said deletion.

7. The method of claim 5 or claim 6 wherein the animal is of the Belgian Blue breed.

8. The method of claim 1 wherein ascertaining whether DNA having a nucleotide sequence encoding a protein having biological activity of myostatin is present includes amplifying the DNA in the presence of a primer containing at least a portion of a naturally occurring mutation and which when present in both alleles of a said animal results in said muscular hyperplasia.

9. A method for determining the presence of muscular hyperplasia in a bovine animal, the method comprising:
    obtaining a sample of the animal containing mRNA; and
    ascertaining whether an mRNA encoding a protein having biological activity of myostatin is present in the sample by amplifying the mRNA in the presence of first and second primers substantially complementary to first and second nucleotide sequences encoding spaced apart regions of the protein, wherein said regions flank a naturally occurring mutation and which when present in both alleles of a said animal results in said muscular hyperplasia,
wherein the absence of said mRNA indicates the presence of muscular hyperplasia in the animal.

10. The method of claim 9 wherein the sample is of muscle tissue.

11. The method of claim 10 wherein the tissue is skeletal muscle tissue.

12. The method of claim 9 wherein ascertaining whether mRNA having a nucleotide sequence encoding a protein having biological activity of myostatin includes amplifying the mRNA in the presence of primers substantially complementary to the nucleotide sequence encoding the protein.

13. The method of claim 12 wherein mRNA of a said bovine animal not displaying muscular hyperplasia has a nucleotide sequence which is capable of hybridizing with a nucleic acid molecule having the sequence identified as SEQ ID NO:1 under stringent hybridization conditions.

14. The method of claim 9, wherein ascertaining whether mRNA having a nucleotide sequence encoding a protein having biological activity of myostatin is present includes amplifying the mRNA in the presence of primers substantially complementary to a nucleotide sequence encoding the N-terminal and the C-terminal, respectively, of the protein having biological activity of myostatin.

15. The method of claim 9 wherein an mRNA of said animal not displaying muscular hyperplasia contains a nucleotide sequence which hybridizes under stringent conditions with a nucleotide sequence encoding a protein having a sequence identified as SEQ ID NO:2 and said first primer is selected to be upstream of the codon encoding glutamic acid no. 275 and the second primer is selected to be downstream of the codon encoding aspartic acid no. 274.

16. The method of claim 9 wherein ascertaining whether mRNA having a nucleotide sequence encoding a protein having biological activity of myostatin is present includes amplifying the mRNA in the presence of a primer containing a nucleotide sequence complementary to at least a portion of a naturally occurring mutation in a said animal and which when present in both alleles of a said animal results in said muscular hyperplasia.

17. The method of claim 16 wherein an mRNA of said animal not displaying muscular hyperplasia contains a nucleotide sequence which hybridizes under stringent conditions with a nucleotide sequence encoding a protein having a sequence identified as SEQ ID NO:2 and the coding sequence of DNA of a said animal displaying muscular hyperplasia is known to contain an 11-base pair deletion beginning at base pair no. 821, and said primer is selected to span the deleted portion.

18. The method of claim 15 or claim 17 wherein the animal is of the Belgian Blue breed.

19. A method for determining the presence of muscular hyperplasia in a mammal, the method comprising:
    obtaining a sample of material containing DNA from the mammal; and
    ascertaining whether (a) a sequence of the DNA encoding a protein having biological activity of myostatin, is present, and whether (b) a naturally occurring sequence of the DNA encoding an allelic protein lacking the activity of a protein having biological activity of myostatin, is present;
wherein the absence of (a) and the presence of (b) indicates the presence of muscular hyperplasia in the mammal.

20. The method of claim 19 wherein the mammal is a human.

21. The method of claim 20 wherein ascertaining whether a sequence of the DNA encoding (a) is present, and whether a sequence of the DNA encoding (b) is present includes amplifying the DNA in the presence of primers based on a nucleotide sequence encoding a protein having biological activity of myostatin.

22. The method of claim 21 wherein said primers are based on the sequence identified as SEQ ID NO:7.

23. A method for determining the presence of muscular hyperplasia in a mammal, the method comprising:
    obtaining a sample of material containing mRNA from the mammal; and
    ascertaining whether (a) a sequence of the mRNA encoding a protein having biological activity of myostatin, is present, and whether (b) a naturally occurring sequence of the mRNA encoding a truncated protein lacking the biological activity of myostatin, is present;
wherein the absence of (a) and the presence of (b) indicates the presence of muscular hyperplasia in the mammal.

24. A method for determining the presence of muscular hyperplasia in a mammal, the method comprising:
    obtaining a tissue sample of containing mRNA of the mammal; and
    ascertaining whether an mRNA encoding a naturally occurring mutant type myostatin protein lacking biological activity of myostatin is present,
wherein the presence of a said mRNA encoding a mutant type myostatin protein indicates the presence of muscular hyperplasia in the mammal.

25. The method of claim 23 wherein the mammal is human.

26. The method of claim 25 wherein ascertaining whether a sequence of (a) is present, and whether a sequence of the mRNA of (b) is present includes amplifying the mRNA in the presence of a pair of primers complementary to a nucleotide sequence encoding a protein having biological activity of myostatin.

27. The method of claim 26 wherein each said primer contains a nucleotide sequence substantially complementary to the sequence identified as SEQ ID NO:7.

28. The method of claim 27 wherein the sequence of (b) contains at least 50 consecutive nucleotides substantially corresponding to 50 consecutive nucleotides of SEQ ID NO:7.

29. The method of claim 23 wherein the mRNA of (a) and the mRNA of (b) correspond to alleles of DNA of the mammal.

30. A method for determining the myostatin genotype of a mammal, comprising:
    obtaining a sample of material containing nucleic acid of the mammal, wherein the nucleic acid is uncontaminated by heterologous nucleic acid;
    ascertaining whether the sample contains a (i) nucleic acid molecule encoding a protein having biological activity of myostatin; and
    ascertaining whether the sample contains a (ii) allelic nucleic acid molecule encoding a naturally occurring protein lacking biological activity of myostatin.

31. The method of claim 30 wherein the mammal is human and (i) comprises a nucleic acid sequence substantially homologous with the sequence identified as SEQ ID NO:7.

32. A method for identifying a nucleotide sequence of a naturally occurring mutant of a gene which normally encodes a myostatin protein, of a mammal displaying muscular hyperplasia, the method comprising:
    obtaining a sample of material containing DNA from the mammal; and
    probing the sample using a nucleic acid probe based on a nucleotide sequence of a known gene encoding myostatin in order to identify the nucleotide sequence of the mutant gene.

33. The method of claim 32, wherein the probe is based on a said nucleotide sequence identified as SEQ ID NO:1, SEQ ID NO:5 or SEQ ID NO:7.

34. The method of claim 33 wherein the probe is based on SEQ ID NO:1 or SEQ ID NO:7.

35. The method of claim 34 wherein the probe is at least 8 nucleic acids in length.

36. The method of claim 32, wherein the step of probing the sample includes exposing the DNA to the probe under hybridizing conditions and further comprising isolating hybridized nucleic acid molecules.

37. The method of claim 36, further comprising the step of sequencing isolated DNA.

38. The method of claim 32, wherein the mammal is a bovine mammal and the probe is based on a said nucleotide sequence identified as SEQ ID NO:1.

39. The method of claim 37, further comprising the step of isolating and sequencing a cDNA or mRNA encoding the complete mutant myostatin protein.

40. The method of claim 39, further comprising the step of isolating and sequencing a functional wild type myostatin from a said mammal not displaying muscular hyperplasia.

41. The method of claim 39, further comprising comparing the complete coding sequence of the complete mutant myostatin protein with, if the coding sequence for a functional wild type myostatin from a said mammal is previously known, (1) the known sequence, or if the coding sequence for a functional wild type myostatin from a said mammal is previously unknown, (2) the sequence determined according to claim 37 or claim 40, to determine the location of any mutation in the mutant gene.

42. A method for determining the myostatin genotype of a mammal, wherein wild type myostatin of the mammal is substantially that of claim 41, comprising:
   obtaining a sample of material containing DNA from the mammal; and
   ascertaining whether the DNA contains a said naturally occurring mutation determined according to claim 41.

43. A method for determining the myostatin genotype of a mammal, wherein wild type myostatin of the mammal is substantially that of claim 41, comprising:
   obtaining a sample of material containing mRNA from the mammal; and
   ascertaining whether the mRNA contains a said mutation determined according to claim 41.

44. The method of claim 6, wherein said primer binds under stringent conditions with a nucleic acid molecule having the sequence identified as SEQ ID NO:3.

45. A method for determining the myostatin genotype of a bovine mammal, comprising:
   obtaining a sample of material containing nucleic acid of the mammal; and
   amplifying the nucleic acid in the presence of a primer having the nucleotide sequence corresponding to a sequence of consecutive nucleotides of the myostatin gene (SEQ ID NO:1) which flank the nucleotide sequence identified as SEQ ID NO:11, in order to determine whether the nucleic acid includes a mutant myostatin coding sequence from which is absent the nucleotide sequence identified as SEQ ID NO:11.

* * * * *

SEQUENCE LISTING (1) GENERAL INFORMATION:

(iii) NUMBER OF SEQUENCES: 52

(2) INFORMATION FOR SEQ ID NO:1:

(i) SEQUENCE CHARACTERISTICS:
        (A) LENGTH: 1196 base pairs
        (B) TYPE: nucleic acid
        (C) STRANDEDNESS: single
        (D) TOPOLOGY: linear (xi) SEQUENCE DESCRIPTION: SEQ ID NO:1:

```
AGGAAAAAGT AAGAACAAGG GAAAAGATTG TATTGATTTT AAAACC ATG CAA AAA              55
                                                 Met Gln Lys
                                                  1

CTG CAA ATC TCT GTT TAT ATT TAC CTA TTT ATG CTG ATT GTT GCT GGC            103
Leu Gln Ile Ser Val Tyr Ile Tyr Leu Phe Met Leu Ile Val Ala Gly
     5               10                  15

CCA GTG GAT CTG AAT GAG AAC AGC GAG CAG AAG GAA AAT GTG CAA AAA            151
Pro Val Asp Leu Asn Glu Asn Ser Glu Gln Lys Glu Asn Val Gln Lys
 20              25                  30                  35

GAG GGG CTG TGT AAT GCA TGT TTG TGG AGG GAA AAC ACT ACA TCC TCA            199
Glu Gly Leu Cys Asn Ala Cys Leu Trp Arg Glu Asn Thr Thr Ser Ser
                 40                  45                  50

AGA CTA GAA GCC ATA AAA ATC CAA ATC CTC AGT AAA CTT CGC CTG GAA            247
Arg Leu Glu Ala Ile Lys Ile Gln Ile Leu Ser Lys Leu Arg Leu Glu
             55                  60                  65

ACA GCT CCT AAC ATC AGC AAA GAT GCT ATC AGA CAA CTT TTG CCC AAG            295
Thr Ala Pro Asn Ile Ser Lys Asp Ala Ile Arg Gln Leu Leu Pro Lys
             70                  75                  80

GCT CCT CCA CTC CTG GAA CTG ATT GAT CAG TTC GAT GTC CAG AGA GAT            343
Ala Pro Pro Leu Leu Glu Leu Ile Asp Gln Phe Asp Val Gln Arg Asp
         85                  90                  95

GCC AGC AGT GAC GGC TCC TTG GAA GAC GAT GAC TAC CAC GCC AGG ACG            391
Ala Ser Ser Asp Gly Ser Leu Glu Asp Asp Asp Tyr His Ala Arg Thr
100                 105                 110                 115

GAA ACG GTC ATT ACC ATG CCC ACG GAG TCT GAT CTT CTA ACG CAA GTG            439
Glu Thr Val Ile Thr Met Pro Thr Glu Ser Asp Leu Leu Thr Gln Val
                120                 125                 130

GAA GGA AAA CCC AAA TGT TGC TTC TTT AAA TTT AGC TCT AAG ATA CAA            487
Glu Gly Lys Pro Lys Cys Cys Phe Phe Lys Phe Ser Ser Lys Ile Gln
            135                 140                 145

TAC AAT AAA CTA GTA AAG GCC CAA CTG TGG ATA TAT CTG AGG CCT GTC            535
Tyr Asn Lys Leu Val Lys Ala Gln Leu Trp Ile Tyr Leu Arg Pro Val
            150                 155                 160

AAG ACT CCT GCG ACA GTG TTT GTG CAA ATC CTG AGA CTC ATC AAA CCC            583
```

-continued

```
Lys Thr Pro Ala Thr Val Phe Val Gln Ile Leu Arg Leu Ile Lys Pro
    165                 170                 175

ATG AAA GAC GGT ACA AGG TAT ACT GGA ATC CGA TCT CTG AAA CTT GAC      631
Met Lys Asp Gly Thr Arg Tyr Thr Gly Ile Arg Ser Leu Lys Leu Asp
180                 185                 190                 195

ATG AAC CCA GGC ACT GGT ATT TGG CAG AGC ATT GAT GTG AAG ACA GTG      679
Met Asn Pro Gly Thr Gly Ile Trp Gln Ser Ile Asp Val Lys Thr Val
                    200                 205                 210

TTG CAG AAC TGG CTC AAA CAA CCT GAA TCC AAC TTA GGC ATT GAA ATC      727
Leu Gln Asn Trp Leu Lys Gln Pro Glu Ser Asn Leu Gly Ile Glu Ile
                215                 220                 225

AAA GCT TTA GAT GAG AAT GGC CAT GAT CTT GCT GTA ACC TTC CCA GAA      775
Lys Ala Leu Asp Glu Asn Gly His Asp Leu Ala Val Thr Phe Pro Glu
            230                 235                 240

CCA GGA GAA GAT GGA CTG ACT CCT TTT TTA GAA GTC AAG GTA ACA GAC      823
Pro Gly Glu Asp Gly Leu Thr Pro Phe Leu Glu Val Lys Val Thr Asp
        245                 250                 255

ACA CCA AAA AGA TCT AGG AGA GAT TTT GGG CTT GAT TGT GAT GAA CAC      871
Thr Pro Lys Arg Ser Arg Arg Asp Phe Gly Leu Asp Cys Asp Glu His
260                 265                 270                 275

TCC ACA GAA TCT CGA TGC TGT CGT TAC CCT CTA ACT GTG GAT TTT GAA      919
Ser Thr Glu Ser Arg Cys Cys Arg Tyr Pro Leu Thr Val Asp Phe Glu
                280                 285                 290

GCT TTT GGA TGG GAT TGG ATT ATT GCA CCT AAA AGA TAT AAG GCC AAT      967
Ala Phe Gly Trp Asp Trp Ile Ile Ala Pro Lys Arg Tyr Lys Ala Asn
                295                 300                 305

TAC TGC TCT GGA GAA TGT GAA TTT GTA TTT TTG CAA AAG TAT CCT CAT     1015
Tyr Cys Ser Gly Glu Cys Glu Phe Val Phe Leu Gln Lys Tyr Pro His
            310                 315                 320

ACC CAT CTT GTG CAC CAA GCA AAC CCC AGA GGT TCA GCC GGC CCC TGC     1063
Thr His Leu Val His Gln Ala Asn Pro Arg Gly Ser Ala Gly Pro Cys
325                 330                 335

TGT ACT CCT ACA AAG ATG TCT CCA ATT AAT ATG CTA TAT TTT AAT GGC     1111
Cys Thr Pro Thr Lys Met Ser Pro Ile Asn Met Leu Tyr Phe Asn Gly
340                 345                 350                 355

GAA GGA CAA ATA ATA TAC GGG AAG ATT CCA GCC ATG GTA GTA GAT CGC     1159
Glu Gly Gln Ile Ile Tyr Gly Lys Ile Pro Ala Met Val Val Asp Arg
                360                 365                 370

TGT GGG TGT TCA TGAGTCTATA TTTGGGTTCA TAAGC                         1196
Cys Gly Cys Ser
            375

(2) INFORMATION FOR SEQ ID NO:2:

(i) SEQUENCE CHARACTERISTICS:
        (A) LENGTH: 375 amino acids
        (B) TYPE: amino acid
        (C) STRANDEDNESS: single
        (D) TOPOLOGY: linear (xi) SEQUENCE DESCRIPTION: SEQ ID NO:2:

Met Gln Lys Leu Gln Ile Ser Val Tyr Ile Tyr Leu Phe Met Leu Ile
1               5                   10                  15

Val Ala Gly Pro Val Asp Leu Asn Glu Asn Ser Glu Gln Lys Glu Asn
            20                  25                  30

Val Glu Lys Glu Gly Leu Cys Asn Ala Cys Leu Trp Arg Glu Asn Thr
        35                  40                  45

Thr Ser Ser Arg Leu Glu Ala Ile Lys Ile Gln Ile Leu Ser Lys Leu
    50                  55                  60

Arg Leu Glu Thr Ala Pro Asn Ile Ser Lys Asp Ala Ile Arg Gln Leu
```

```
                65                     70                     75                     80
Leu Pro Lys Ala Pro Pro Leu Glu Leu Ile Asp Gln Phe Asp Val
                        85                     90                     95
Gln Arg Asp Ala Ser Ser Asp Gly Ser Leu Glu Asp Asp Tyr His
                100                    105                    110
Ala Arg Thr Glu Thr Val Ile Thr Met Pro Thr Glu Ser Asp Leu Leu
                115                    120                    125
Thr Gln Val Glu Gly Lys Pro Lys Cys Cys Phe Phe Lys Phe Ser Ser
    130                    135                    140
Lys Ile Gln Tyr Asn Lys Leu Val Lys Ala Gln Leu Trp Ile Tyr Leu
145                    150                    155                    160
Arg Pro Val Lys Thr Pro Ala Thr Val Phe Val Gln Ile Leu Arg Leu
                165                    170                    175
Ile Lys Pro Met Lys Asp Gly Thr Arg Tyr Thr Gly Ile Arg Ser Leu
                180                    185                    190
Lys Leu Asp Met Asn Pro Gly Thr Gly Ile Trp Gln Ser Ile Asp Val
                195                    200                    205
Lys Thr Val Leu Gln Asn Trp Leu Lys Gln Pro Glu Ser Asn Leu Gly
                210                    215                    220
Ile Glu Ile Lys Ala Leu Asp Glu Asn Gly His Asp Leu Ala Val Thr
225                    230                    235                    240
Phe Pro Glu Pro Gly Glu Asp Gly Leu Thr Pro Phe Leu Glu Val Lys
                245                    250                    255
Val Thr Asp Thr Pro Lys Arg Ser Arg Arg Asp Phe Gly Leu Asp Cys
                260                    265                    270
Asp Glu His Ser Thr Glu Ser Arg Cys Cys Arg Tyr Pro Leu Thr Val
            275                    280                    285
Asp Phe Glu Ala Phe Gly Trp Asp Trp Ile Ile Ala Pro Lys Arg Tyr
    290                    295                    300
Lys Ala Asn Tyr Cys Ser Gly Glu Cys Glu Phe Val Phe Leu Gln Lys
305                    310                    315                    320
Tyr Pro His Thr His Leu Val His Gln Ala Asn Pro Arg Gly Ser Ala
                325                    330                    335
Gly Pro Cys Cys Thr Pro Thr Lys Met Ser Pro Ile Asn Met Leu Tyr
            340                    345                    350
Phe Asn Gly Glu Gly Gln Ile Ile Tyr Gly Lys Ile Pro Ala Met Val
    355                    360                    365
Val Asp Arg Cys Gly Cys Ser
    370                    375

(2) INFORMATION FOR SEQ ID NO:3:

(i) SEQUENCE CHARACTERISTICS:
        (A) LENGTH: 1240 base pairs
        (B) TYPE: nucleic acid
        (C) STRANDEDNESS: single
        (D) TOPOLOGY: linear (xi) SEQUENCE DESCRIPTION: SEQ ID NO:3:

AGGAAAAAGT AAGAACAAGG GAAAAGATTG TATTGATTTT AAAACC ATG CAA AAA             55
                                                   Met Gln Lys
                                                     1

CTG CAA ATC TCT GTT TAT ATT TAC CTA TTT ATG CTC ATT GTT GCT GGC          103
Leu Gln Ile Ser Val Tyr Ile Tyr Leu Phe Met Leu Ile Val Ala Gly
      5                  10                  15

CCA GTG GAT CTG AAT GAG AAC AGC GAG CAG AAG GAA AAT GTG GAA AAA          151
```

-continued

```
Pro Val Asp Leu Asn Glu Asn Ser Glu Gln Lys Glu Asn Val Glu Lys
 20              25                  30                  35

GAG GGG CTG TGT AAT GCA TGT TTG TGG AGG GAA AAC ACT ACA TCC TCA         199
Glu Gly Leu Cys Asn Ala Cys Leu Trp Arg Glu Asn Thr Thr Ser Ser
                 40                  45                  50

AGA CTA GAA GCC ATA AAA ATC CAA ATC CTC AGT AAA CTT CGC CTG GAA         247
Arg Leu Glu Ala Ile Lys Ile Gln Ile Leu Ser Lys Leu Arg Leu Glu
             55                  60                  65

ACA GCT CCT AAC ATC AGC AAA GAT GCT ATC AGA CAA CTT TTG CCC AAG         295
Thr Ala Pro Asn Ile Ser Lys Asp Ala Ile Arg Gln Leu Leu Pro Lys
         70                  75                  80

GCT CCT CCA CTC CTG GAA CTG ATT GAT CAG TTC GAT GTC CAG AGA GAT         343
Ala Pro Pro Leu Leu Glu Leu Ile Asp Gln Phe Asp Val Gln Arg Asp
     85                  90                  95

GCC AGC AGT GAC GGC TCC TTG GAA GAC GAT GAC TAC CAC GCC AGG ACG         391
Ala Ser Ser Asp Gly Ser Leu Glu Asp Asp Asp Tyr His Ala Arg Thr
100                 105                 110                 115

GAA ACG GTC ATT ACC ATG CCC ACG GAG TCT GAT CTT CTA ACG CAA GTG         439
Glu Thr Val Ile Thr Met Pro Thr Glu Ser Asp Leu Leu Thr Gln Val
                 120                 125                 130

GAA GGA AAA CCC AAA TGT TGC TTC TTT AAA TTT AGC TCT AAG ATA CAA         487
Glu Gly Lys Pro Lys Cys Cys Phe Phe Lys Phe Ser Ser Lys Ile Gln
             135                 140                 145

TAC AAT AAA CTA GTA AAG GCC CAA CTG TGG ATA TAT CTG AGG CCT GTC         535
Tyr Asn Lys Leu Val Lys Ala Gln Leu Trp Ile Tyr Leu Arg Pro Val
         150                 155                 160

AAG ACT CCT GCG ACA GTG TTT GTG CAA ATC CTC AGA CTC ATC AAA CCC         583
Lys Thr Pro Ala Thr Val Phe Val Gln Ile Leu Arg Leu Ile Lys Pro
     165                 170                 175

ATG AAA GAC GGT ACA AGG TAT ACT GGA ATC CGA TCT CTG AAA CTT GAC         631
Met Lys Asp Gly Thr Arg Tyr Thr Gly Ile Arg Ser Leu Lys Leu Asp
180                 185                 190                 195

ATG AAC CCA GGC ACT GGT ATT TGG CAG AGC ATT GAT GTG AAG ACA GTG         679
Met Asn Pro Gly Thr Gly Ile Trp Gln Ser Ile Asp Val Lys Thr Val
                 200                 205                 210

TTG CAG AAC TGG CTC AAA CAA CCT GAA TCC AAC TTA GGC ATT GAA ATC         727
Leu Gln Asn Trp Leu Lys Gln Pro Glu Ser Asn Leu Gly Ile Glu Ile
             215                 220                 225

AAA GCT TTA GAT GAG AAT GGC CAT GAT CTT GCT GTA ACC TTC CCA GAA         775
Lys Ala Leu Asp Glu Asn Gly His Asp Leu Ala Val Thr Phe Pro Glu
         230                 235                 240

CCA GGA GAA GAT GGA CTG ACT CCT TTT TTA GAA GTC AAG GTA ACA GAC         823
Pro Gly Glu Asp Gly Leu Thr Pro Phe Leu Glu Val Lys Val Thr Asp
     245                 250                 255

ACA CCA AAA AGA TCT AGG AGA GAT TTT GGG CTT GAT TGT GAC AGA ATC         871
Thr Pro Lys Arg Ser Arg Arg Asp Phe Gly Leu Asp Cys Asp Arg Ile
260                 265                 270                 275

TCG ATG CTG TCG TTA CCC TCT AAC TGT GGA TTT TGAAGCTTTT                  914
Ser Met Leu Ser Leu Pro Ser Asn Cys Gly Phe
                 280                 285

GGATGGGATT GGATTATTGC ACCTAAAAGA TATAAGGCCA ATTACTGCTC TGGAGAATGT       974

GAATTTGTAT TTTTGCAAAA GTATCCTCAT ACCCATCTTG TGCACCAAGC AAACCCAGA        1034

GGTTCAGCCG GCCCCTGCTG TACTCCTACA AAGATGTCTC CAATTAATAT GCTATATTTT       1094

AATGGCGAAG GACAAATAAT ATACGGGAAG ATTCCAGCCA TGGTAGTAAA TCGCTGTGGG       1154

TGTTCATGAG GTCTATATTT GGTTCATAGC TTCCTCAAAC ATGGAAGGTC TTCCCCTCAA       1214

CAATTTTGAA ACTGTTGAAA TTATGT                                            1240
```

(2) INFORMATION FOR SEQ ID NO:4:

(i) SEQUENCE CHARACTERISTICS:
        (A) LENGTH: 286 amino acids
        (B) TYPE: amino acid
        (C) STRANDEDNESS: single
        (D) TOPOLOGY: linear (xi) SEQUENCE DESCRIPTION: SEQ ID NO:4:

```
Met Gln Lys Leu Gln Ile Ser Val Tyr Ile Tyr Leu Phe Met Leu Ile
 1               5                  10                  15

Val Ala Gly Pro Val Asp Leu Asn Glu Asn Ser Glu Gln Lys Glu Asn
            20                  25                  30

Val Glu Lys Glu Gly Leu Cys Asn Ala Cys Leu Trp Arg Glu Asn Thr
        35                  40                  45

Thr Ser Ser Arg Leu Glu Ala Ile Lys Ile Gln Ile Leu Ser Lys Leu
    50                  55                  60

Arg Leu Glu Thr Ala Pro Asn Ile Ser Lys Asp Ala Ile Arg Gln Leu
65                  70                  75                  80

Leu Pro Lys Ala Pro Pro Leu Leu Glu Leu Ile Asp Gln Phe Asp Val
                85                  90                  95

Gln Arg Asp Ala Ser Ser Asp Gly Ser Leu Glu Asp Asp Tyr His
            100                 105                 110

Ala Arg Thr Glu Thr Val Ile Thr Met Pro Thr Glu Ser Asp Leu Leu
        115                 120                 125

Thr Gln Val Glu Gly Lys Pro Lys Cys Cys Phe Phe Lys Phe Ser Ser
    130                 135                 140

Lys Ile Gln Tyr Asn Lys Leu Val Lys Ala Gln Leu Trp Ile Tyr Leu
145                 150                 155                 160

Arg Pro Val Lys Thr Pro Ala Thr Val Phe Val Gln Ile Leu Arg Leu
                165                 170                 175

Ile Lys Pro Met Lys Asp Gly Thr Arg Tyr Thr Gly Ile Arg Ser Leu
            180                 185                 190

Lys Leu Asp Met Asn Pro Gly Thr Gly Ile Trp Gln Ser Ile Asp Val
        195                 200                 205

Lys Thr Val Leu Gln Asn Trp Leu Lys Gln Pro Glu Ser Asn Leu Gly
    210                 215                 220

Ile Glu Ile Lys Ala Leu Asp Glu Asn Gly His Asp Leu Ala Val Thr
225                 230                 235                 240

Phe Pro Glu Pro Gly Glu Asp Gly Leu Thr Pro Phe Leu Glu Val Lys
                245                 250                 255

Val Thr Asp Thr Pro Lys Arg Ser Arg Arg Asp Phe Gly Leu Asp Cys
            260                 265                 270

Asp Arg Ile Ser Met Leu Ser Leu Pro Ser Asn Cys Gly Phe
        275                 280                 285
```

(2) INFORMATION FOR SEQ ID NO:5:

(i) SEQUENCE CHARACTERISTICS:
        (A) LENGTH: 2676 base pairs
        (B) TYPE: nucleic acid
        (C) STRANDEDNESS: single
        (D) TOPOLOGY: linear (xi) SEQUENCE DESCRIPTION: SEQ ID NO:5:

```
GTCTCTCGGA CGGTACATGC ACTAATATTT CACTTGGCAT TACTCAAAAG CAAAAAGAAG      60

AAATAAGAAC AAGCGAAAAA AAAGATTGT GCTGATTTTT AAA ATG ATG CAA AAA       115
```

```
                                            Met Met Gln Lys
                                              1

CTG CAA ATG TAT GTT TAT ATT TAC CTC TTC ATG CTG ATT GCT GCT GGC       163
Leu Gln Met Tyr Val Tyr Ile Tyr Leu Phe Met Leu Ile Ala Ala Gly
 5           10                  15                      20

CCA GTG GAT CTA AAT GAG GGC AGT GAG AGA GAA GAA AAT GTG GAA AAA       211
Pro Val Asp Leu Asn Glu Gly Ser Glu Arg Glu Glu Asn Val Glu Lys
                 25                  30                  35

GAG GGG CTG TGT AAT GCA TGT GCG TGG AGA CAA AAC ACG AGG TAC TCC       259
Glu Gly Leu Cys Asn Ala Cys Ala Trp Arg Gln Asn Thr Arg Tyr Ser
             40                  45                  50

AGA ATA GAA GCC ATA AAA ATT CAA ATC CTC AGT AAG CTG CGC CTG GAA       307
Arg Ile Glu Ala Ile Lys Ile Gln Ile Leu Ser Lys Leu Arg Leu Glu
         55                  60                  65

ACA GCT CCT AAC ATC AGC AAA GAT GCT ATA AGA CAA CTT CTG CCA AGA       355
Thr Ala Pro Asn Ile Ser Lys Asp Ala Ile Arg Gln Leu Leu Pro Arg
     70                  75                  80

GCG CCT CCA CTC CGG GAA CTG ATC GAT CAG TAC GAC GTC CAG AGG GAT       403
Ala Pro Pro Leu Arg Glu Leu Ile Asp Gln Tyr Asp Val Gln Arg Asp
 85              90                  95                  100

GAC AGC AGT GAT GGC TCT TTG GAA GAT GAC GAT TAT CAC GCT ACC ACG       451
Asp Ser Ser Asp Gly Ser Leu Glu Asp Asp Asp Tyr His Ala Thr Thr
                 105                 110                 115

GAA ACA ATC ATT ACC ATG CCT ACA GAG TCT GAC TTT CTA ATG CAA GCG       499
Glu Thr Ile Ile Thr Met Pro Thr Glu Ser Asp Phe Leu Met Gln Ala
             120                 125                 130

GAT GGC AAG CCC AAA TGT TGC TTT TTT AAA TTT AGC TCT AAA ATA CAG       547
Asp Gly Lys Pro Lys Cys Cys Phe Phe Lys Phe Ser Ser Lys Ile Gln
         135                 140                 145

TAC AAC AAA GTA GTA AAA GCC CAA CTG TGG ATA TAT CTC AGA CCC GTC       595
Tyr Asn Lys Val Val Lys Ala Gln Leu Trp Ile Tyr Leu Arg Pro Val
     150                 155                 160

AAG ACT CCT ACA ACA GTG TTT GTG CAA ATC CTG AGA CTC ATC AAA CCC       643
Lys Thr Pro Thr Thr Val Phe Val Gln Ile Leu Arg Leu Ile Lys Pro
165                 170                 175                 180

ATG AAA GAC GGT ACA AGG TAT ACT GGA ATC CGA TCT CTG AAA CTT GAC       691
Met Lys Asp Gly Thr Arg Tyr Thr Gly Ile Arg Ser Leu Lys Leu Asp
                 185                 190                 195

ATG AGC CCA GGC ACT GGT ATT TGG CAG AGT ATT GAT GTG AAG ACA GTG       739
Met Ser Pro Gly Thr Gly Ile Trp Gln Ser Ile Asp Val Lys Thr Val
             200                 205                 210

TTG CAA AAT TGG CTC AAA CAG CCT GAA TCC AAC TTA GGC ATT GAA ATC       787
Leu Gln Asn Trp Leu Lys Gln Pro Glu Ser Asn Leu Gly Ile Glu Ile
         215                 220                 225

AAA GCT TTG GAT GAG AAT GGC CAT GAT CTT GCT GTA ACC TTC CCA GGA       835
Lys Ala Leu Asp Glu Asn Gly His Asp Leu Ala Val Thr Phe Pro Gly
230                 235                 240

CCA GGA GAA GAT GGG CTG AAT CCC TTT TTA GAA GTC AAG GTG ACA GAC       883
Pro Gly Glu Asp Gly Leu Asn Pro Phe Leu Glu Val Lys Val Thr Asp
245                 250                 255                 260

ACA CCC AAG AGG TCC CGG AGA GAC TTT GGG CTT GAC TGC GAT GAG CAC       931
Thr Pro Lys Arg Ser Arg Arg Asp Phe Gly Leu Asp Cys Asp Glu His
                 265                 270                 275

TCC ACG GAA TCC CGG TGC TGC CGC TAC CCC CTC ACG GTC GAT TTT GAA       979
Ser Thr Glu Ser Arg Cys Cys Arg Tyr Pro Leu Thr Val Asp Phe Glu
             280                 285                 290

GCC TTT GGA TGG GAC TGG ATT ATC GCA CCC AAA AGA TAT AAG GCC AAT      1027
Ala Phe Gly Trp Asp Trp Ile Ile Ala Pro Lys Arg Tyr Lys Ala Asn
         295                 300                 305
```

```
TAC TGC TCA GGA GAG TGT GAA TTT GTG TTT TTA CAA AAA TAT CCG CAT      1075
Tyr Cys Ser Gly Glu Cys Glu Phe Val Phe Leu Gln Lys Tyr Pro His
            310                 315                 320

ACT CAT CTT GTG CAC CAA GCA AAC CCC AGA GGC TCA GCA GGC CCT TGC      1123
Thr His Leu Val His Gln Ala Asn Pro Arg Gly Ser Ala Gly Pro Cys
325                 330                 335                 340

TGC ACT CCG ACA AAA ATG TCT CCC ATT AAT ATG CTA TAT TTT AAT GGC      1171
Cys Thr Pro Thr Lys Met Ser Pro Ile Asn Met Leu Tyr Phe Asn Gly
                345                 350                 355

AAA GAA CAA ATA ATA TAT GGC AAA ATT CCA GCC ATG GTA GTA GAC CGC      1219
Lys Glu Gln Ile Ile Tyr Gly Lys Ile Pro Ala Met Val Val Asp Arg
            360                 365                 370

TGT GGG TGC TCA TGAGCTTTGC ATTAGGTTAG AAACTTCCCA AGTCATGGAA          1271
Cys Gly Cys Ser
        375

GGTCTTCCCC TCAATTTCGA AACTGTGAAT TCAAGCACCA CAGGCTGTAG GCCTTGAGTA    1331

TGCTCTACTA ACGTAAGCAC AAGCTACAGT GTATGAACTA AAAGAGAGAA TAGATGCAAT    1391

GGTTGGCATT CAACCACCAA AATAAACCAT ACTATAGGAT GTTGTATGAT TTCCAGAGTT    1451

TTTGAAATAG ATGGAGATCA AATTACATTT ATGTCCATAT ATGTATATTA CAACTACAAT    1511

CTAGGCAAGG AAGTGAGAGC ACATCTTGTG GTCTGCTGAG TTAGGAGGGT ATGATTAAAA    1571

GGTAAAGTCT TATTTCCTAA CAGTTTCACT TAATATTTAC AGAACAATCT ATATGTAGCC    1631

TTTGTAAAGT GTAGGATTGT TATCATTTAA AAACATCATG TACACTTATA TTTGTATTGT    1691

ATACTTGGTA AGATAAAATT CCACAAAGTA GGAATGGGGC CTCACATACA CATTGCCATT    1751

CCTATTATAA TTGGACAATC CACCACGGTG CTAATGCAGT GCTCAATGGC TCCTACTGGA    1811

CCTCTCGATA GAACACTCTA CAAAGTACGA GTCTCTCTCT CCCTTCCAGG TGCATCTCCA    1871

CACACACAGC ACTAAGTGTT CAATGCATTT TCTTTAAGGA AAGAAGAATC TTTTTTTCTA    1931

GAGGTCAACT TTCAGTCAAC TCTAGCACAG CGGGAGTGAC TGCTGCATCT TAAAAGGCAG    1991

CCAAACAGTA TTCATTTTTT AATCTAAATT TCAAAATCAC TGTCTGCCTT TATCACATGG    2051

CAATTTTGTG GTAAAATAAT GGAAATGACT GGTTCTATCA ATATTGTATA AAAGACTCTG    2111

AAACAATTAC ATTTATATAA TATGTATACA ATATTGTTTT GTAAATAAGT GTCTCCTTTT    2171

ATATTTACTT TGGTATATTT TTACACTAAT GAAATTTCAA ATCATTAAAG TACAAAGACA    2231

TGTCATGTAT CACAAAAAAG GTGACTGCTT CTATTTCAGA GTGAATTAGC AGATTCAATA    2291

GTGGTCTTAA AACTCTGTAT GTTAAGATTA GAAGGTTATA TTACAATCAA TTTATGTATT    2351

TTTTACATTA TCAACTTATG GTTTCATGGT GGCTGTATCT ATGAATGTGG CTCCCAGTCA    2411

AATTTCAATG CCCCACCATT TTAAAAATTA CAAGCATTAC TAAACATACC AACATGTATC    2471

TAAAGAAATA CAAATATGGT ATCTCAATAA CAGCTACTTT TTTATTTTAT AATTTGACAA    2531

TGAATACATT TCTTTTATTT ACTTCAGTTT TATAAATTGG AACTTTGTTT ATCAAATGTA    2591

TTGTACTCAT AGCTAAATGA AATTATTTCT TACATAAAAA TGTGTAGAAA CTATAAATTA    2651

AAGTGTTTTC ACATTTTTGA AAGGC                                         2676
```

(2) INFORMATION FOR SEQ ID NO:6:

(i) SEQUENCE CHARACTERISTICS:
        (A) LENGTH: 376 amino acids
        (B) TYPE: amino acid
        (C) STRANDEDNESS: single
        (D) TOPOLOGY: linear (xi) SEQUENCE DESCRIPTION: SEQ ID NO:6:

```
Met Met Gln Lys Leu Gln Met Tyr Val Tyr Ile Tyr Leu Phe Met Leu
 1               5                  10                  15

Ile Ala Ala Gly Pro Val Asp Leu Asn Glu Gly Ser Glu Arg Glu Glu
             20                  25                  30

Asn Val Glu Lys Glu Gly Leu Cys Asn Ala Cys Ala Trp Arg Gln Asn
         35                  40                  45

Thr Arg Tyr Ser Arg Ile Glu Ala Ile Lys Ile Gln Ile Leu Ser Lys
     50                  55                  60

Leu Arg Leu Glu Thr Ala Pro Asn Ile Ser Lys Asp Ala Ile Arg Gln
 65                  70                  75                  80

Leu Leu Pro Arg Ala Pro Pro Leu Arg Glu Leu Ile Asp Gln Tyr Asp
                 85                  90                  95

Val Gln Arg Asp Asp Ser Ser Asp Gly Ser Leu Glu Asp Asp Asp Tyr
            100                 105                 110

His Ala Thr Thr Glu Thr Ile Ile Thr Met Pro Thr Glu Ser Asp Phe
            115                 120                 125

Leu Met Gln Ala Asp Gly Lys Pro Lys Cys Cys Phe Phe Lys Phe Ser
130                 135                 140

Ser Lys Ile Gln Tyr Asn Lys Val Lys Ala Gln Leu Trp Ile Tyr
145                 150                 155                 160

Leu Arg Pro Val Lys Thr Pro Thr Thr Val Phe Val Gln Ile Leu Arg
            165                 170                 175

Leu Ile Lys Pro Met Lys Asp Gly Thr Arg Tyr Thr Gly Ile Arg Ser
            180                 185                 190

Leu Lys Leu Asp Met Ser Pro Gly Thr Gly Ile Trp Gln Ser Ile Asp
        195                 200                 205

Val Lys Thr Val Leu Gln Asn Trp Leu Lys Gln Pro Glu Ser Asn Leu
210                 215                 220

Gly Ile Glu Ile Lys Ala Leu Asp Glu Asn Gly His Asp Leu Ala Val
225                 230                 235                 240

Thr Phe Pro Gly Pro Gly Glu Asp Gly Leu Asn Pro Phe Leu Glu Val
            245                 250                 255

Lys Val Thr Asp Thr Pro Lys Arg Ser Arg Arg Asp Phe Gly Leu Asp
            260                 265                 270

Cys Asp Glu His Ser Thr Glu Ser Arg Cys Cys Arg Tyr Pro Leu Thr
275                 280                 285

Val Asp Phe Glu Ala Phe Gly Trp Asp Trp Ile Ile Ala Pro Lys Arg
290                 295                 300

Tyr Lys Ala Asn Tyr Cys Ser Gly Glu Cys Glu Phe Val Phe Leu Gln
305                 310                 315                 320

Lys Tyr Pro His Thr His Leu Val His Gln Ala Asn Pro Arg Gly Ser
                325                 330                 335

Ala Gly Pro Cys Cys Thr Pro Lys Met Ser Pro Ile Asn Met Leu
            340                 345                 350

Tyr Phe Asn Gly Lys Glu Gln Ile Ile Tyr Gly Lys Ile Pro Ala Met
            355                 360                 365

Val Val Asp Arg Cys Gly Cys Ser
370                 375

(2) INFORMATION FOR SEQ ID NO:7:

(i) SEQUENCE CHARACTERISTICS:
        (A) LENGTH: 2215 base pairs
        (B) TYPE: nucleic acid
        (C) STRANDEDNESS: single
```

(D) TOPOLOGY: linear (xi) SEQUENCE DESCRIPTION: SEQ ID NO:7:

```
NGATTTTCTA ATGCAAGTGG ATGGAAAACC CAAATGTTGC TTCTTTAAAT TTAGCTCTAA      60
AATACAATAC AATAAAGTAG TAAAGGCCCA ACTATCCATA TATTTGAGAC CCGTCGAGAC     120
TCCTACAACA GTGTTTGTGC AAATCCTGAG ACTCATCAAA CCTATGAAAG ACGGTACAAG     180
GTATCTGGAA TCCGATCTCT GAAACTTGAC ATGAACCCAG GCACTGGTAT TTGGGCAGAN     240
ATTGATGTGA AGACACTGTT GCAAAATTGG CTCAAACAAC CTGAATCCAA CTTAGGCATT     300
GAAATAAAAG CTTTACATGA GAATGGTCAT GATCTTGCTG TAACCTTCCC AGGACCAGGA     360
AGAAGATGGG CTGAATCCCT TTTTTAAGAA GGTCAAGGTA ACAGACACAC CAAAAAGATT     420
CCAGAAGGGA TTTTGGGTCT TGACTGGTGA TGAGCACTCA ACAGAATCAC GATCCTGTCG     480
TTACCCCCTA ACTGGTGGAT TTTGAAGCCT TTGGGATGGG ATTGGATATC GNNNNNNNNN     540
NNNNNNNNNN NNNNNNNNNN NNNNNNNNNN NNNNNNNNNN NNNNNNNNNN NNNNNNNNNN     600
NNNNNNNNNN NNNNNNNNNN NNNNNNNNNN NNNNNNNNNN NNNNNNNNNN NNNNNNNNNN     660
NNNNNNNNNN NNNNNNNNNN NNNNNNNNNN NNNNNNNNNN NNNNNNNNNN NNNNNNNNNN     720
NNNNNNNNNN NAGCGATGGT AGTAGACCGC TGTGGGTGCT CAGCGATGGT AGTAGACCGC     780
TGTGGGTGCT CTTTTCAAGC TGTGAAATTA AGTACCACAG GCTATAGGCC TAGAGTATGC     840
TACAGTCACT TAAGCATAAG CTACAGTATG TAAACTAAAA GGGGGAAGG GAATATATGC      900
AATGGTTGGC ATTTAACCAT CCAAACAAAT CATACCAGAA AGTTTTATGA TTTCCANAGT     960
TTTTTNAGGC NAGAAAGGAG GAGTCAAANT TTCANTCTTA TGGTNNNNNN NNNNNNNNNN    1020
NNNNNNNNNN NNNNNNNNNN NNNNNNNNNN NNNNNNNNNN NNNNNNNNNN NNNNNNNNNN    1080
NNNNNNNNNN NNNNNNNNNN NNNNNNNNNN NNNNNNNNNN NNNNNNNNNN NNNNNNNNNN    1140
NNNNNNNNNN NNNNNNNNNN NNNNNNNNNN NNNNATTTCG GCACAGGTNA AACACTTGAA    1200
TTTATATTGT ATGGTAGTAT ACTTGGTAAG ATAAAATTCC ACAAAAATAG GGATGGTGCA    1260
GCATATGCAA TTTCCATTCC TATTATAATT GACACAGTAC ATTAACAATC CATGCCAACG    1320
GTGCTAATAC GATAGGCTGA NNNNNNNNNN NNNNNNNNNN NNNNNNNNNN NNNNNNNNNN    1380
NNNNNNNNNN NNNNNNNNNN NNNNNNNNNN NNNNNNNNNN NNNNNNNNNN NNNNNNNNNN    1440
NNNNNNNNNN NNNNNNNNNN NNNNNNNNNN NNNNNNNNNN NNNNNNNNNN NNNNNNNNNN    1500
NNNNNNNNNN NNNNNNNNNN NNNNNNNNNN NNNNNNNNNN NNNNNNNNNN NNNNNNNNNN    1560
NNNNNNNNNN NNNNNNNNNN NNNNNNNNNN NNNNNNNNNN NNNNNNNNNN NNNNNNNNNN    1620
NNNNNNNNNN NNNNNNNNNN NNNNNNNNNN NNNNNNNNNN NNNNNNNNNN NNNNNNNNNN    1680
NNNNNNNNNN NNNNNNNNNN NNNNNNNNNN NNNNNNNNNN NNNNNNNNNN NNNNNNNNNN    1740
NNNNNNNNNN NNNNNNNNNN NNNNNNNNNN NNNNNNNNNN NNNNNNNNNN NNNNNNNNNN    1800
NNNNNNNNNN NNNNNNNNNN NNNNNNNNNN NNNNNNNNNN NNNNNNNNNN NNNNNNNNNN    1860
NNNNNNNNNN NNNNNNNNNN NNNNNNNNNN NNNNNNNNNN NNNNNNNNNN NNNNNNNNNN    1920
TAAATCTCAA CGTTCCATTA TTTTAATACT TGCAAAAACA TTACTAAGTA TACCAAAATA    1980
ATTGACTCTA TTATCTGAAA TGAAGAATAA ACTGATGCTA TCTCAACAAT AACTGTTACT    2040
TTTATTTTAT AATTTGATAA TGAATATATT TCTGCATTTA TTTACTTCTG TTTTGTAAAT    2100
TGGGATTTTG TTAATCAAAT TTATTGTACT ATGACTAAAT GAAATTATTT CTTACATCTA    2160
ATTTGTAGAA ACAGTATAAG TTATATTAAA GTGTTTTCAC ATTTTTTTGA AAGAC         2215
```

(2) INFORMATION FOR SEQ ID NO:8:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:8:

ATACTCWAGG CCTAYAGCCT GTGGT                                         25

(2) INFORMATION FOR SEQ ID NO:9:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:9:

GGCCCAACTA TGGATATATT TG                                           22

(2) INFORMATION FOR SEQ ID NO:10:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:10:

GGTCCTGGGA AGGTTACAGC A                                            21

(2) INFORMATION FOR SEQ ID NO:11:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (xi) SEQUENCE DESCRIPTION: SEQ ID NO:11:

ATGAACACTC C                                                                    11

(2) INFORMATION FOR SEQ ID NO:12:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:12:

CAGCAAAGTC CTTAATGGTA ACAAGC                                      26

(2) INFORMATION FOR SEQ ID NO:13:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:13:

GGGTCACTGA AGAAAACGTC CTG                                          23

(2) INFORMATION FOR SEQ ID NO:14:

(i) SEQUENCE CHARACTERISTICS:
              (A) LENGTH: 23 base pairs
              (B) TYPE: nucleic acid
              (C) STRANDEDNESS: single
              (D) TOPOLOGY: linear (xi) SEQUENCE DESCRIPTION: SEQ ID NO:14:

CCCCATATTA TGGAGATGAA CCG                                                  23

(2) INFORMATION FOR SEQ ID NO:15:

(i) SEQUENCE CHARACTERISTICS:
              (A) LENGTH: 23 base pairs
              (B) TYPE: nucleic acid
              (C) STRANDEDNESS: single
              (D) TOPOLOGY: linear (xi) SEQUENCE DESCRIPTION: SEQ ID NO:15:

AGTTCAGGAT GGCAGAATTT CAG                                                  23

(2) INFORMATION FOR SEQ ID NO:16:

(i) SEQUENCE CHARACTERISTICS:
              (A) LENGTH: 23 base pairs
              (B) TYPE: nucleic acid
              (C) STRANDEDNESS: single
              (D) TOPOLOGY: linear (xi) SEQUENCE DESCRIPTION: SEQ ID NO:16:

GCAAACTGGG YGGRAGCAAG ACC                                                  23

(2) INFORMATION FOR SEQ ID NO:17:

(i) SEQUENCE CHARACTERISTICS:
              (A) LENGTH: 24 base pairs
              (B) TYPE: nucleic acid
              (C) STRANDEDNESS: single
              (D) TOPOLOGY: linear (xi) SEQUENCE DESCRIPTION: SEQ ID NO:17:

TTSTTCCTGG GCTTTTATTG AGAC                                                 24

(2) INFORMATION FOR SEQ ID NO:18:

(i) SEQUENCE CHARACTERISTICS:
              (A) LENGTH: 25 base pairs
              (B) TYPE: nucleic acid
              (C) STRANDEDNESS: single
              (D) TOPOLOGY: linear (xi) SEQUENCE DESCRIPTION: SEQ ID NO:18:

AAGCCWGATT TCTGCTTYTT GGAAG                                               25

(2) INFORMATION FOR SEQ ID NO:19:

(i) SEQUENCE CHARACTERISTICS:
              (A) LENGTH: 25 base pairs
              (B) TYPE: nucleic acid
              (C) STRANDEDNESS: single
              (D) TOPOLOGY: linear (xi) SEQUENCE DESCRIPTION: SEQ ID NO:19:

TGCCMAGGCA HCCRCCRTAC TTGAA                                                25

(2) INFORMATION FOR SEQ ID NO:20:

```
    (i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:20:

GGTCGTCCTA CACCAGAAG                                                 19

(2) INFORMATION FOR SEQ ID NO:21:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:21:

GGTTGACATT GTCAAGAACA AG                                             22

(2) INFORMATION FOR SEQ ID NO:22:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:22:

TCTCMAAAGT CGTCTGTGAC AATC                                           24

(2) INFORMATION FOR SEQ ID NO:23:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:23:

TGYTCRTTTT CTTTCAGAGT TGC                                            23

(2) INFORMATION FOR SEQ ID NO:24:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:24:

RCTGGTCCTC TTCACCTCAG AAC                                           23

(2) INFORMATION FOR SEQ ID NO:25:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:25:

ACATTGTCVG TTCCAAAGCC AAG                                            23

(2) INFORMATION FOR SEQ ID NO:26:

(i) SEQUENCE CHARACTERISTICS:
```

```
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:26:

AGGTYCGGGT GACDGTGCTK C                                              21

(2) INFORMATION FOR SEQ ID NO:27:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:27:

TGGRTACATG AGYTCCACCT TGC                                            23

(2) INFORMATION FOR SEQ ID NO:28:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:28:

AGCTGCARGT ATWCCTACAA YCT                                            23

(2) INFORMATION FOR SEQ ID NO:29:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:29:

GTYCCRTTGC TCYTCTCRTT GYC                                            23

(2) INFORMATION FOR SEQ ID NO:30:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:30:

AACTGTATAT TGAGAGCCTA CCATG                                          25

(2) INFORMATION FOR SEQ ID NO:31:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:31:

CACACCTTAG CGACTAAACC ACCA                                           24

(2) INFORMATION FOR SEQ ID NO:32:

(i) SEQUENCE CHARACTERISTICS:
        (A) LENGTH: 25 base pairs
```

(B) TYPE: nucleic acid
        (C) STRANDEDNESS: single
        (D) TOPOLOGY: linear (xi) SEQUENCE DESCRIPTION: SEQ ID NO:32:

CTACCTAACA GAATGATTTT GTAAG                                    25

(2) INFORMATION FOR SEQ ID NO:33:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:33:

AGTGTTCTTG CCTAGAGAAT CCCAG                                    25

(2) INFORMATION FOR SEQ ID NO:34:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:34:

ACATTCTCTC ACCAATATGA CATAC                                    25

(2) INFORMATION FOR SEQ ID NO:35:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:35:

TAAGTCACCA TTACATCCTT AGAAC                                    25

(2) INFORMATION FOR SEQ ID NO:36:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:36:

GCTGTAAGAA TCTTCATTAA GCACT                                    25

(2) INFORMATION FOR SEQ ID NO:37:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:37:

CCTGATACAT GCTAAGGTTA AAAAC                                    25

(2) INFORMATION FOR SEQ ID NO:38:

(i) SEQUENCE CHARACTERISTICS:
        (A) LENGTH: 25 base pairs
        (B) TYPE: nucleic acid (C) STRANDEDNESS: single
        (D) TOPOLOGY: linear (xi) SEQUENCE DESCRIPTION: SEQ ID NO:38:

AGGCATACAT CTGGAGAGAA ACATG                                              25

(2) INFORMATION FOR SEQ ID NO:39:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:39:

CAGAGGAGCC TAGCAGGCTA CCGTC                                              25

(2) INFORMATION FOR SEQ ID NO:40:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:40:

CAGCAGGTCT GTTGAAGTGT ATCAG                                              25

(2) INFORMATION FOR SEQ ID NO:41:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:41:

AGTGGTAGCA TTCACAGGTA GCCAG                                              25

(2) INFORMATION FOR SEQ ID NO:42:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:42:

CAGTCCATGG CACCATAAAG                                                    20

(2) INFORMATION FOR SEQ ID NO:43:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:43:

TCCGTTAGTA CTGGCTAATT GC                                                 22

(2) INFORMATION FOR SEQ ID NO:44:

(i) SEQUENCE CHARACTERISTICS:
        (A) LENGTH: 20 base pairs
        (B) TYPE: nucleic acid
        (C) STRANDEDNESS: single (D) TOPOLOGY: linear (xi) SEQUENCE DESCRIPTION: SEQ ID NO:44:

CTGAATTGGC TCCAAAGGCC                                                    20

(2) INFORMATION FOR SEQ ID NO:45:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:45:

AAACAGAAGT CCAGGGCTGC                                                    20

(2) INFORMATION FOR SEQ ID NO:46:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (xi) SEQUENCE DESCRIPTION: SEQ ID NO:46:

TCAGTCTCCA GGAGAGAAAA C                                                  21

(2) INFORMATION FOR SEQ ID NO:47:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:47:

CTCTGCCCTG GGGATGATTG                                                    20

(2) INFORMATION FOR SEQ ID NO:48:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (xi) SEQUENCE DESCRIPTION: SEQ ID NO:48:

AATGTATGTT TATATTTACC TGTTCATG                                           28

(2) INFORMATION FOR SEQ ID NO:49:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (xi) SEQUENCE DESCRIPTION: SEQ ID NO:49:

ACAGTGTTTG TGCAAATCCT GAGAC                                              25

(2) INFORMATION FOR SEQ ID NO:50:

(i) SEQUENCE CHARACTERISTICS:
            (A) LENGTH: 25 base pairs
            (B) TYPE: nucleic acid
            (C) STRANDEDNESS: single
            (D) TOPOLOGY: linear -continued

```
    (xi) SEQUENCE DESCRIPTION: SEQ ID NO:50:

CAATGCCTAA GTTGGATTCA GGTTG                                              25

(2) INFORMATION FOR SEQ ID NO:51:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:51:

CTTGCTGTAA CCTTCCCAGG ACCAG                                              25

(2) INFORMATION FOR SEQ ID NO:52:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:52:

TCCCATCCAA AGGCTTCAAA ATC                                                23
```